United States Patent
Everett et al.

(10) Patent No.: US 8,705,048 B2
(45) Date of Patent: *Apr. 22, 2014

(54) SPECTRAL DOMAIN OPTICAL COHERENCE TOMOGRAPHY SYSTEM

(71) Applicant: Carl Zeiss Meditec, Inc., Dublin, CA (US)

(72) Inventors: Matthew J. Everett, Livermore, CA (US); Martin Hacker, Jena (DE)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/857,675

(22) Filed: Apr. 5, 2013

(65) Prior Publication Data

US 2013/0287277 A1    Oct. 31, 2013

Related U.S. Application Data

(60) Continuation of application No. 13/312,245, filed on Dec. 6, 2011, now Pat. No. 8,427,654, which is a division of application No. 12/842,935, filed on Jul. 23, 2010, now Pat. No. 8,085,408, which is a division of application No. 11/820,773, filed on Jun. 20, 2007, now abandoned.

(60) Provisional application No. 60/925,104, filed on Apr. 18, 2007, provisional application No. 60/815,107, filed on Jun. 20, 2006.

(51) Int. Cl.
*G01B 11/02*    (2006.01)

(52) U.S. Cl.
USPC .......................................... 356/497

(58) Field of Classification Search
USPC .................................. 356/479, 497
See application file for complete search history.

(56) References Cited

U.S. PATENT DOCUMENTS

| | | | |
|---|---|---|---|
| 4,252,420 | A | 2/1981 | Kohayakawa |
| 5,321,501 | A | 6/1994 | Swanson et al. |
| 5,459,570 | A | 10/1995 | Swanson et al. |
| 5,465,147 | A | 11/1995 | Swanson |

(Continued)

FOREIGN PATENT DOCUMENTS

| | | |
|---|---|---|
| WO | 01/95791 A1 | 12/2001 |
| WO | 2005/033624 A1 | 4/2005 |

OTHER PUBLICATIONS

Bashkansky et al., "Statistics and Reduction of Speckle in Optical Coherence Tomography", Optics Letters, vol. 25, No. 8, Apr. 15, 2000, pp. 545-547.

(Continued)

*Primary Examiner* — Tarifur Chowdhury
*Assistant Examiner* — Jonathon Cook
(74) *Attorney, Agent, or Firm* — Morrison & Foerster LLP

(57) ABSTRACT

An optical coherence tomography device is disclosed for improved imaging. Reduced levels of speckle in the images generated by the device are obtained by forming a B-scan from a plurality of A-scans, wherein each resolution cell of the B-scan is generated through compounding of a subset of the A-scans and wherein at least some of the subset of A-scans are separated by at least half the diameter of a speckle cell both tangent to and orthogonal to the B-scan at that cell.

32 Claims, 21 Drawing Sheets

(56) References Cited

U.S. PATENT DOCUMENTS

| | | | |
|---|---|---|---|
| 5,537,126 | A | 7/1996 | Kayser et al. |
| 5,537,162 | A | 7/1996 | Hellmuth et al. |
| 5,570,182 | A | 10/1996 | Nathel et al. |
| 5,633,974 | A | 5/1997 | Chia |
| 5,847,827 | A * | 12/1998 | Fercher ......................... 356/493 |
| 6,095,648 | A | 8/2000 | Birngruber et al. |
| 6,201,608 | B1 | 3/2001 | Mandella et al. |
| 6,263,096 | B1 | 7/2001 | Boag et al. |
| 6,595,643 | B2 | 7/2003 | Levine |
| 6,654,127 | B2 | 11/2003 | Everett et al. |
| 6,657,727 | B1 | 12/2003 | Izatt et al. |
| 6,847,449 | B2 | 1/2005 | Bashkansky et al. |
| 6,992,776 | B2 | 1/2006 | Feldchtein et al. |
| 7,236,251 | B2 | 6/2007 | Takaoka |
| 7,330,273 | B2 | 2/2008 | Podoleanu et al. |
| 7,768,652 | B2 | 8/2010 | Everett |
| 7,791,734 | B2 | 9/2010 | Olivier et al. |
| 7,830,525 | B2 | 11/2010 | Buckland et al. |
| 8,134,554 | B1 * | 3/2012 | Huang et al. .................. 345/424 |
| 2002/0048025 | A1 | 4/2002 | Takaoka |
| 2004/0066489 | A1 | 4/2004 | Benedikt et al. |
| 2005/0231727 | A1 | 10/2005 | Podoleanu et al. |
| 2005/0254009 | A1 | 11/2005 | Baker et al. |
| 2006/0039004 | A1 | 2/2006 | de Boer et al. |
| 2006/0119858 | A1 | 6/2006 | Knighton et al. |
| 2006/0164653 | A1 | 7/2006 | Everett et al. |
| 2006/0171503 | A1 | 8/2006 | O'Hara et al. |
| 2006/0228011 | A1 | 10/2006 | Everett et al. |
| 2007/0030483 | A1 | 2/2007 | Everett et al. |
| 2007/0076217 | A1 | 4/2007 | Baker et al. |
| 2007/0103693 | A1 | 5/2007 | Everett et al. |
| 2007/0216909 | A1 | 9/2007 | Everett et al. |
| 2007/0291277 | A1 | 12/2007 | Everett et al. |

OTHER PUBLICATIONS

Boppart et al., "Ultrahigh Resolution and Spectroscopic OCT Imaging of Cellular Morphology and Function", Proc. Inter-Institute Workshop on In Vivo Optical Imaging at the National Institutes of Health, 1999, 7 pages.

Bouma et al., "Power-Efficient Nonreciprocal Interferometer and Linear-Scanning Fiber-Optics Catheter for Optical Coherence Tomography", Optics Letters, vol. 24, No. 8, Apr. 15, 1999, pp. 531-533.

Choma et al., "Senstivity Advantage of Swept Source and Fourier Domain Optical Coherence Tomography", Optical Express, vol. 11, No. 18, 2003, pp. 2183-2189.

Collett, E. "Polarization Controllers", Polarized Light in Fiber Optics, Chapter 9, published by Polawave Group, 2003, pp. 183-226.

Czerwinski et al., "Line and Boundary Detection in Speckle Images", IEEE Transactions on Image Processing, vol. 7, No. 12, Dec. 1998, pp. 1700-1714.

de Boer et al., "Improved signal-to-noise ratio in spectral-domain compared with time-domain optical coherence tomography", Optics Letters, vol. 28, No. 21, Nov. 1, 2003, pp. 2067-2069.

Fernandez et al., "Influence of Ocular Chromatic Aberration and Pupil Size on Transverse Resolution in Ophthalmic Adaptive Optics Optical Coherence Tomography", Optics Express, vol. 13, No. 20, Oct. 3, 2005, pp. 8184-8197.

Hausler et al., "'Coherence Radar' and 'Spectral Radar'—New Tools for Dermatological Diagnosis", Journal of Biomedical Optics, vol. 3, No. 1, Jan. 1998, pp. 21-31.

Hausler et al., "Observation of Light Propagation in Volume Scatters with 10(11)-Fold Slow Motion", Optics Letters, vol. 21, No. 14, Jul. 15, 1996, pp. 1087-1089.

Hee et al., "Optical Coherence Tomography for Ophthalmic Imaging: New Technique Delivers Micron-Scale Resolution", IEEE Engineering in Medicine and Biology, Jan./Feb. 1995, pp. 67-76.

Izatt et al., "Micrometer-Scale Resolution Imaging of the Anterior Eye in Vivo with Optical Coherence Tomography", Arch Ophthalmol, vol. 112, Dec. 1994, pp. 1584-1589.

Jorgensen et al., "Reducing Speckle Noise in Retinal OCT Images by Aligning Multiple B-Scans", Proc. of SPIE, vol. 5316, 2004, pp. 205-213.

Kalev-Landoy et al., "Optical Coherence Tomography in Anterior Segment Imaging", Acta Ophthalmol Scand, vol. 85, No. 4, Jun. 2007, 8 pages.

Kholodnykh et al., "Precision of Measurement of tissue Optical Properties with Optical Coherence Tomography", Applied Optics, vol. 42, No. 16, Jun. 1, 2003, pp. 3027-3037.

Leitgeb et al., "Performance of Fourier Domain vs. Time Domain Optical Coherence Tomography", Optics Express, vol. 11, No. 8, Apr. 21, 2003, pp. 889-894.

Leung et al., "Visualization of Anterior Chamber Angle Dynamics Using Optical Coherence Tomography", Ophthalmology, vol. 112, Jun. 2005, pp. 980-984.

Podoleanu et al., "En-face Coherence Imaging using Galvanometer Scanner Modulation", Optics Letters, vol. 23, No. 3, Feb. 1, 1998, pp. 147-148.

Schmitt et al., "Speckle in Optical Coherence Tomography", Journal of Biomedical Optics, vol. 4, No. 1, Jan. 1999, pp. 95-105.

Smith et al., "Absolute Displacement Measurements using Modulation of the Spectrum of White Light in a Michelson Interferometer", Applied Optics, vol. 28, No. 15, Aug. 15, 1989, pp. 3339-3342.

Wojtkowski et al., "Three-Dimensional Retinal Imaging with High-Speed Ultrahigh-Resolution Optical Coherence Tomography", Ophthalmology, Oct. 2005, pp. 1734-1746.

Yun et al., "Motion Artifacts in Optical Coherence Tomography with Frequency-Domain Ranging", Optics Express, vol. 12, No. 13, Jun. 28, 2004, pp. 2977-2998.

Zawadzki et al., "Adaptive-Optics Optical Coherence Tomography for High-Resolution and High-Speed 3D Retinal in Vivo Imaging", Optics Express, vol. 13, No. 21, Oct. 17, 2005, pp. 8532-8546.

Non Final Office Action received for U.S. Appl. No. 11/820,773, mailed on Apr. 26, 2010, 16 pages.

Non Final Office Action received for U.S. Appl. No. 12/842,935, mailed on Mar. 4, 2011, 11 pages.

Notice of Allowance received for U.S. Appl. No. 12/842,935, mailed on Aug. 30, 2011, 8 pages.

Non Final Office Action received for U.S. Appl. No. 13/312,245, mailed on Jun. 12, 2012, 8 pages.

Final Office Action received for U.S. Appl. No. 13/312,245 mailed on Oct. 12, 2012, 10 pages.

Notice of Allowance received for U.S. Appl. No. 13/312,245, mailed on Dec. 26, 2012, 4 pages.

* cited by examiner

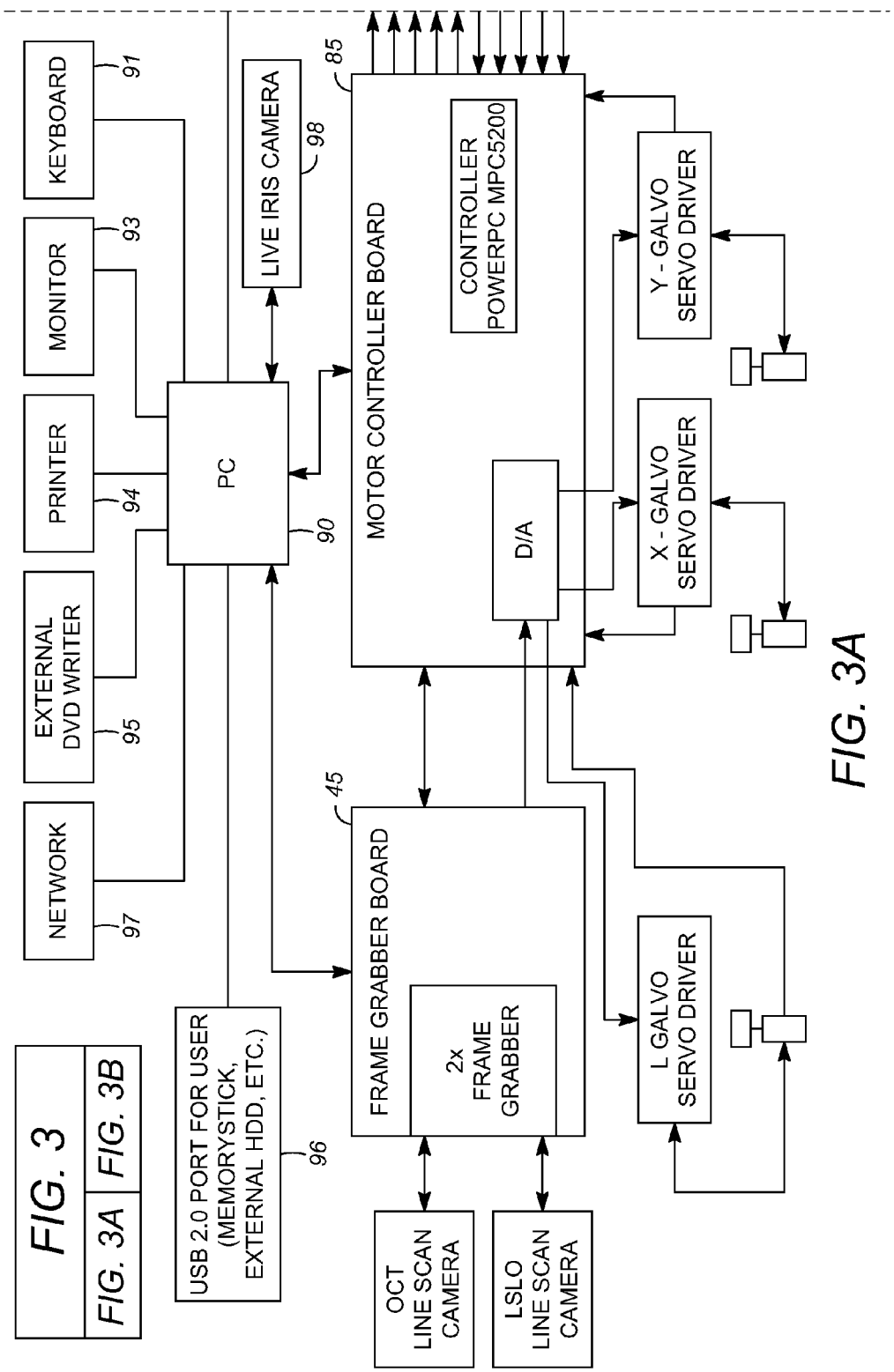

DESIGN OF THE POLARIZATION PADDLE

AN INTERNAL TEST TARGET

FLOW CHART OF SCAN STATES DURING THE OPERATION OF THE INSTRUMENT

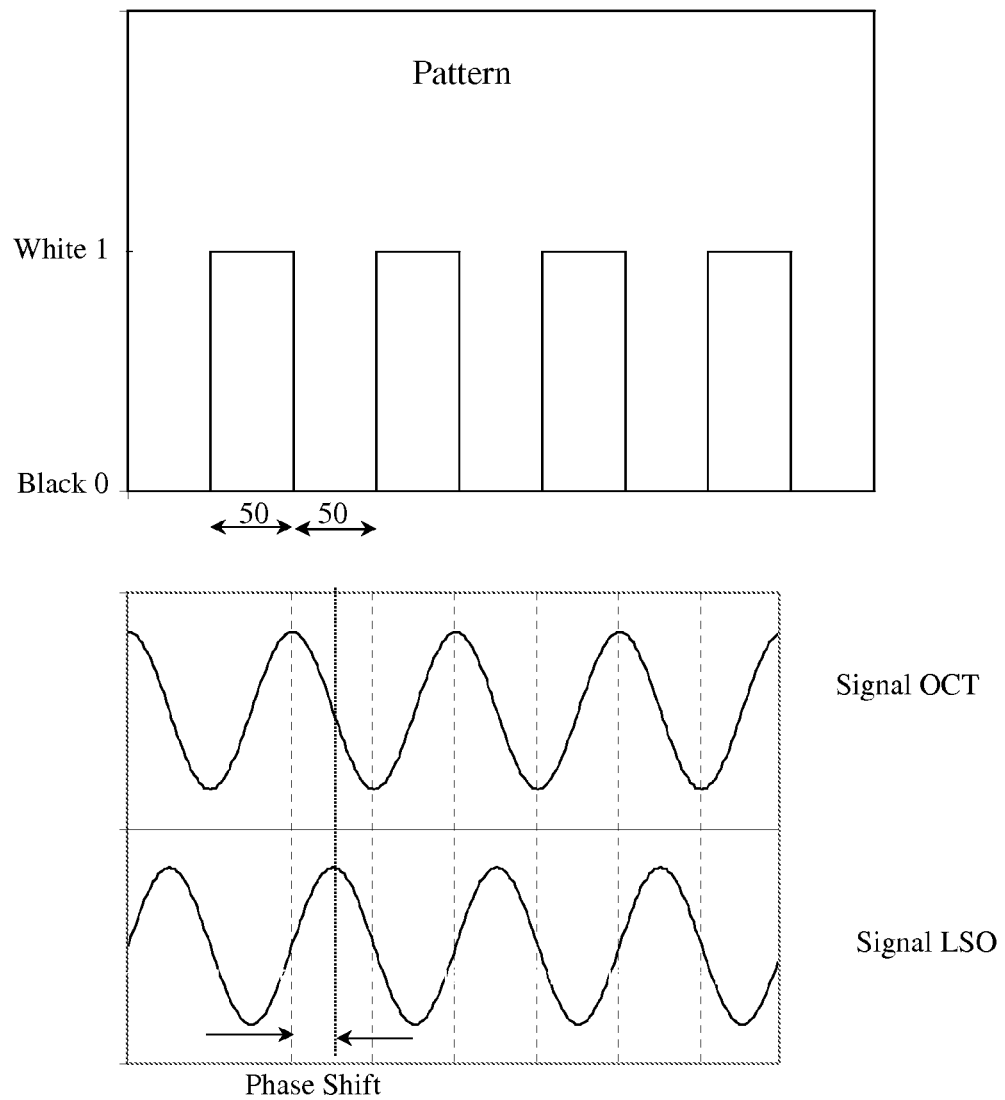
Fig. 7: Analysis of the internal test target.

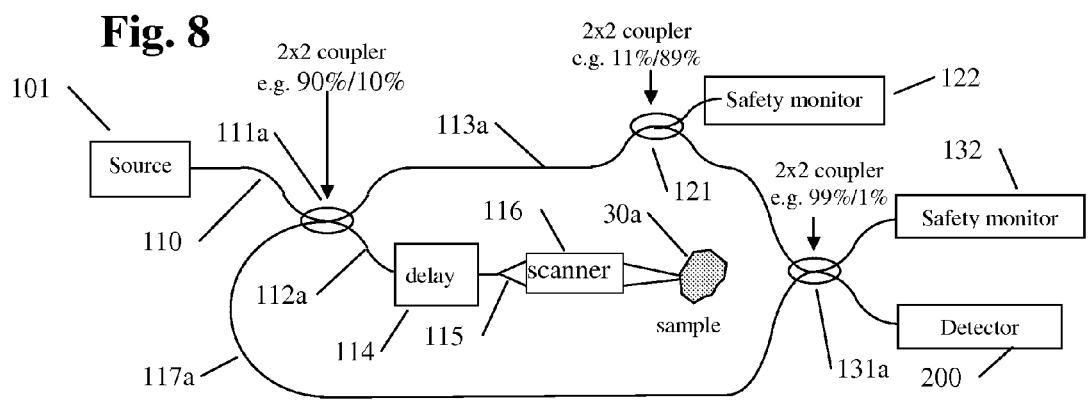
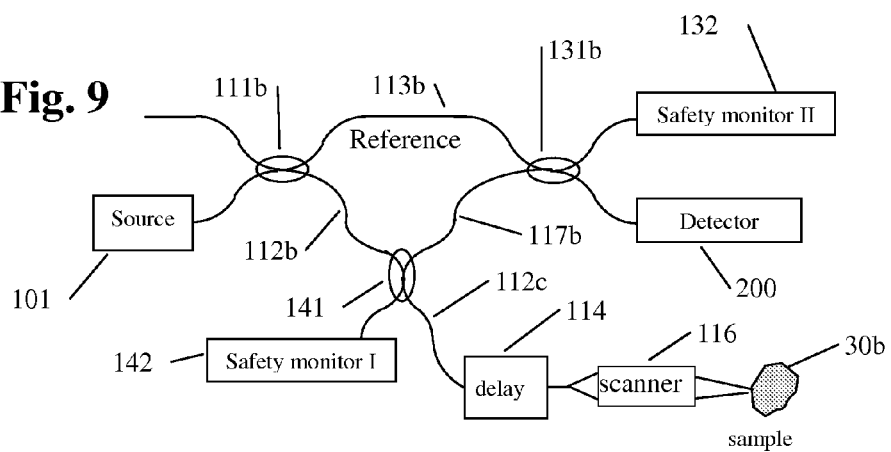

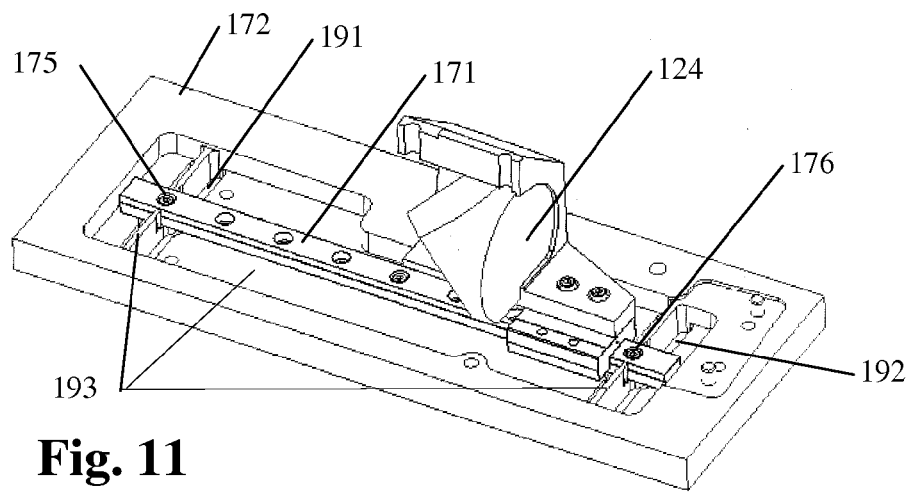
Fig. 11
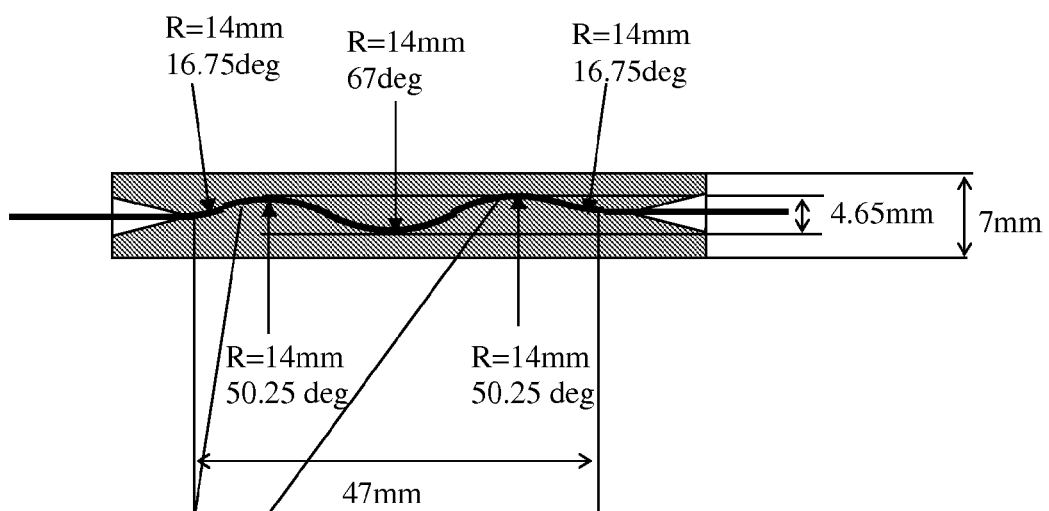
Fig. 12
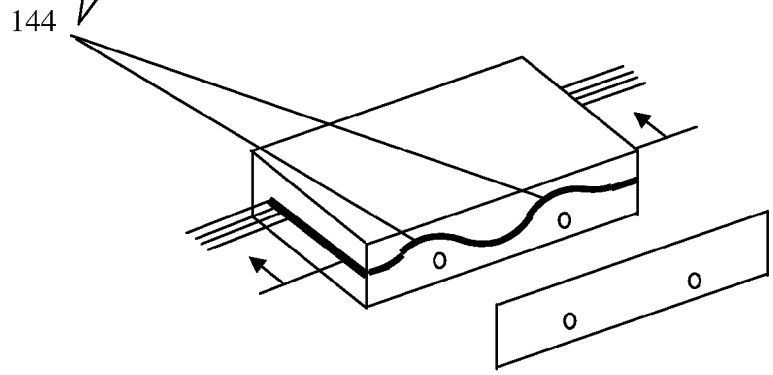

| FIG. 14A | FIG. 14AA |
|---|---|
|  | FIG. 14AB |

| ALIGNMENT STEP | SKETCH | MOTOR MOVEMENT | DISPLAY / UI CONTROL | AID / FEEDBACK |
|---|---|---|---|---|
| 1. MOVE EYE / CHINREST TO HOME POSITION |  | CHINREST x, y, z OCULAR LENS | PRESS ON "HOME" BUTTON |  |
| 2. PATIENT PUTS HEAD IN CHINREST | EYE (MOTORIZED CHINREST)<br>-22.5mm +26.0mm 35.0mm +44.0mm<br>NOMINAL POSITION / NOMINAL POSITION | N/A | LOOK AT PATIENT |  |
| 3. MOVE CHINREST FORWARD TO BRING IRIS IMAGE IN FOCUS AND CENTER IRIS (SET WORKING DISTANCE) | EYE (MOTORIZED CHINREST)<br>-22.5mm +26.0mm 35.0mm +44.0mm<br>NOMINAL POSITION / NOMINAL POSITION | CHINREST x, y, z | LIVE IRIS VIEWER | AUTO-CENTRATION AND AUTO-FOCUS, OR OBJECTIVE SOFTWARE FEEDBACK |

FIG. 14AA

| ALIGNMENT STEP | SKETCH | MOTOR MOVEMENT | DISPLAY / UI CONTROL | AID / FEEDBACK |
|---|---|---|---|---|
| 3.5 (OPTIONAL) SET PATIENT'S PRESCRIPTION (SPHERE ONLY) | EYE (MOTORIZED CHINREST)<br>-22.5mm +26.0mm NOMINAL POSITION<br>35.0mm +44.0mm POSITION | OCULAR LENS | ENTER PRESCRIPTION | |
| 6.5 (OPTIONAL) ADJUST OCULAR LENS POSITION TO OPTIMIZE OCT IMAGE BRIGHTNESS | EYE (MOTORIZED CHINREST)<br>-22.5mm +26.0mm NOMINAL POSITION<br>35.0mm +44.0mm POSITION | OCULAR LENS | OCT IMAGE | |

FIG. 14B

*Prior Art*

SPECTRAL DOMAIN OPTICAL COHERENCE TOMOGRAPHY SYSTEM

PRIORITY

This application is a continuation of U.S. application Ser. No. 13/312,245, filed Dec. 6, 2011, which is a divisional of U.S. application Ser. No. 12/842,935, filed Jul. 23, 2010 (now U.S. Pat. No. 8,085,408), which is a divisional of U.S. application Ser. No. 11/820,773, filed Jun. 20, 2007. This application claims the benefit of the filing date under 35 U.S.C. §119(e) of Provisional U.S. Patent Application Ser. No. 60/815,107, filed on Jun. 20, 2006, and Provisional U.S. Patent Application Ser. No. 60/925,104, filed on Apr. 18, 2007, which are hereby incorporated by reference in their entirety.

TECHNICAL FIELD OF THE INVENTION

The subject invention relates to diagnostic and measurement devices for evaluating a patient's eye. In particular, a spectral domain optical coherence tomography system is disclosed.

BACKGROUND OF THE INVENTION

Optical Coherence Tomography (OCT) is a technology for performing high-resolution cross sectional imaging that can provide images of tissue structure on the micron scale in situ and in real time. OCT is a method of interferometry that uses light containing a range of optical frequencies to determine the scattering profile of a sample. Optical coherence tomography (OCT) as a tool for evaluating biological materials was first disclosed in the early 1990's (see U.S. Pat. No. 5,321,501 for fundus imaging.). Since that time, a number of manufacturers have released products based on this technology. For example, the assignee herein markets a device called the StratusOCT. This device is used for diagnostic imaging and provides direct cross sectional images of the retina for objective measurement and subjective clinical evaluation in the detection of glaucoma and retinal diseases. The device can generate images of macular thickness, the retinal nerve fiber layer, the optic disc, the cornea, and other parts of the eye. This device is based on a version of OCT known as time domain OCT.

In recent years, it has been demonstrated that frequency domain OCT has significant advantages in speed and signal to noise ratio as compared to time domain OCT (Leitgeb, R. A., et al., *Optics Express* 11:889-894; de Boer, J. F. et al., *Optics Letters* 28: 2067-2069; Choma, M. A., and M. V. Sarunic, *Optics Express* 11: 2183-2189).

In frequency domain OCT, a light source capable of emitting a range of optical frequencies excites an interferometer, the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of Frequency domain OCT have been described in the literature. In spectral-domain OCT (SD-OCT), also sometimes called "Spectral Radar" (*Optics letters*, Vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, *Applied Optics* 28: 3339-3342), wherein the distance to a scatterer is determined by the wavelength dependent fringe spacing within the power spectrum. SD-OCT has enabled the determination of distance and scattering intensity of multiple scatters lying along the illumination axis by analyzing a single the exposure of an array of optical detectors so that no scanning in depth is necessary. Typically the light source emits a broad range of optical frequencies simultaneously. Alternatively, in swept-source OCT, the interference spectrum is recorded by using a source with adjustable optical frequency, with the optical frequency of the source swept through a range of optical frequencies, and recording the interfered light intensity as a function of time during the sweep (U.S. Pat. No. 5,321,501).

The commercial OCT systems typically include some form of scanning minor configuration to scan the light beam across the eye in a plane perpendicular to the propagation axis of the beam. The most common interferometer configuration for OCT is the Michelson interferometer [FIG. 1a of U.S. Pat. No. 5,321,501]. Michelson interferometers return some reference arm light to the source, causing a conflict between the desire to set the reference level for best performance of the detector, and to set the reference level low enough to be below the back-reflection tolerance. Some alternative interferometer topologies allow the reference path to be completely in fiber, allowing simple construction. If the reference path is completely in fiber then the sample path length can be varied instead (U.S. Pat. No. 5,321,501).

Non-reciprocal optical elements in the source arm [U.S. Pat. No. 6,657,727 issued to Izatt, et al.] have been used to divert the reflected light that would otherwise return to the source to a detector. While this protects the source and increases its longevity, non-reciprocal optical elements in the source arm add significant costs to the interferometer manufacture.

Interferometers with topology different from the common Michelson topology have been proposed for OCT (U.S. Pat. No. 5,321,501 FIG. 10, U.S. Pat. No. 6,201,608 issued to Mandella, et al., and U.S. Pat. No. 6,992,776 issued to Feldchtein, et al.). Some of these designs route the reference light without retro-reflecting or otherwise reversing the reference light back toward the source. In such interferometer designs some light returned from the sample can reach the source, but this is less of a concern because in many applications only a small fraction ($10^{-4}$ to $10^{-10}$) of the incident light is scattered from the sample and returned to the interferometer.

There has been a continuing effort in the industry to improve the existing OCT systems. For example, when measuring living tissue such as an eye, movement during the measurement period can cause a wide variety of difficulties. Efforts have been made to increase the speed of data collection to reduce the effects of motion of the subject. In addition, various approaches have been suggested to measure sample motion and then compensate for that motion.

BRIEF DESCRIPTION OF THE DRAWINGS

FIGS. 3a and 3b are a two-part electrical block diagram of the PC and system peripherals.

FIG. 7 illustrates analysis of the internal test target.

FIG. 8 illustrates one topology of an interferometer for OCT.

FIG. 9 illustrates another topology of an interferometer for OCT.

FIG. 11 illustrates a mounting block for the corner cube rail.

FIG. 12 illustrates an embodiment for bending fiber as a method of birefringence compensation.

FIG. 14aa covers steps 1 to 3 while FIG. 14ab covers steps 4 to 9.

FIG. 14b is a table of optional steps used for alignment of an OCT imaging system.

DISCLOSURE OF THE INVENTION

This document is intended to describe a new OCT system being developed by the assignee herein. The principals and applications of the invention are set forth in part in the description which follows, and, in part, will be obvious to those skilled in the art from the description provided herein. Further advantages may be learned by practice of the invention. The scope of the invention is defined by the claims, which includes known equivalents and unforeseeable equivalents at the time of filing of this application. This new system is a spectral domain optical coherence tomographer including a spectrometer. The system also includes a line scanning ophthalmoscope (LSO) and an iris viewing system. Certain aspects of the individual sub-systems are unique. In addition, the combination of these sub-systems is also unique.

Some of the inventive concepts being employed in the subject OCT system have been described in earlier filed patent applications which will be referenced herein all of which are incorporated by reference. This disclosure is intended to describe the overall system.

Figure 1:
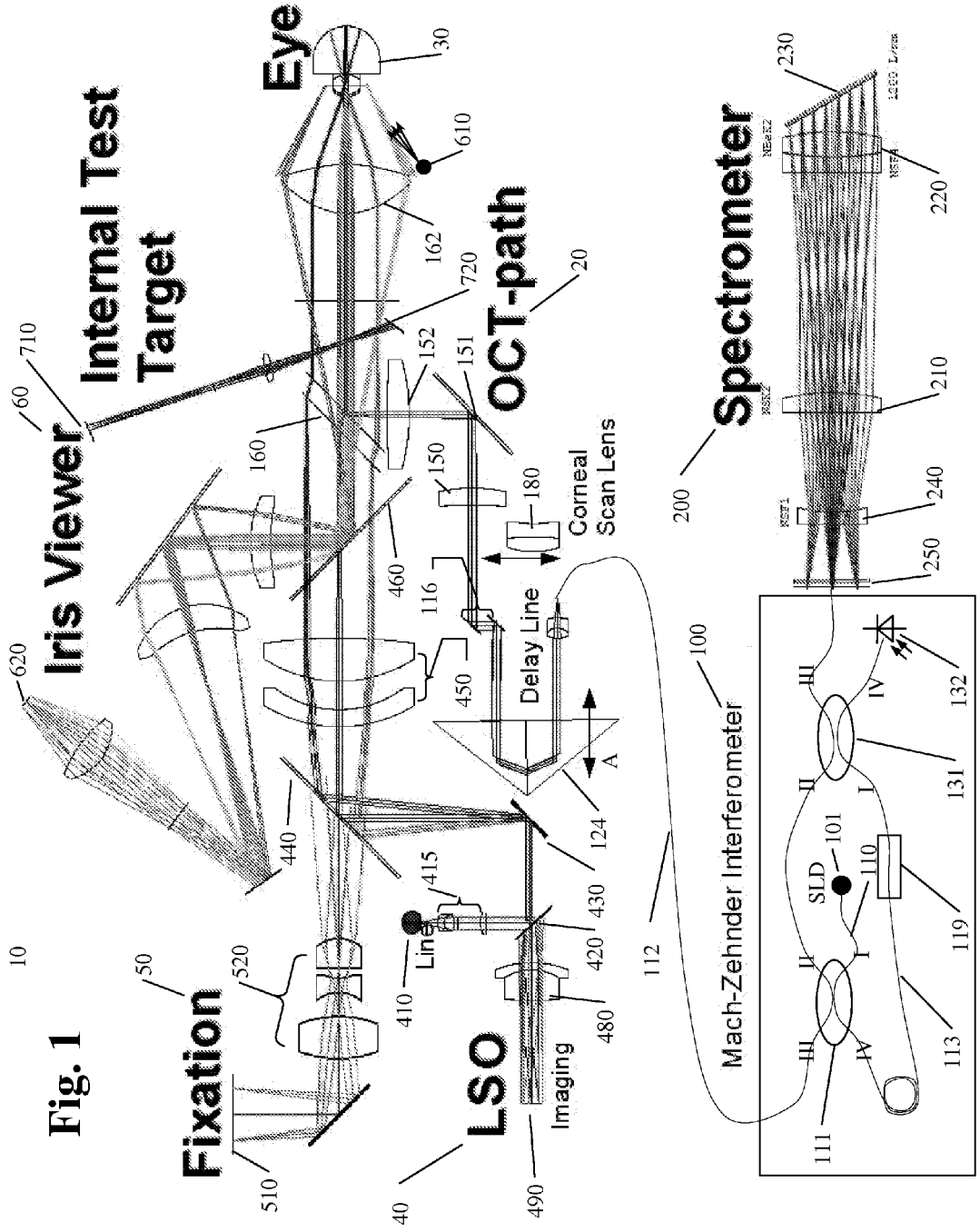
FIG. 1 is an optical path system diagram including the OCT path, the LSO path, the Fixation path, the Iris Viewer path, and the internal test target path.

FIG. 1 is a schematic of the principal optical components of the system 10 specially designed to generate diagnostic images of an eye 30. The system 10 includes four primary sub-systems, an optical coherent tomography (OCT) system 20, a line scanning ophthalmoscope (LSO) 40, a fixation system 50, and an iris viewer 60.

The OCT system is a spectral domain system generally of the type described in the above-cited articles. The OCT system 20 includes a low coherence light source 101 which in this case is a super luminescent diode that has bandwidth of about 800 to 900 nm with a center wavelength of 840 nm. One choice for this device is the SD371 manufactured by Superlum Diodes in Moscow. The output from the SLD 101 is directed into a fiber based interferometer 100. An input fiber 110 is connected to a first port I of a 70/30 optical coupler 111. The coupler 34 directs thirty percent of the light out of port III to the sample arm fiber 112 and seventy percent of the light out of port IV to the reference arm fiber 113. The reference arm fiber 113 is optionally connected to an optical attenuator 119. An optical attenuator is useful for attenuating excess signal passing through the reference arm. A variable optical attenuator can also compensate for the variability of other components. In particular, a variable optical attenuator can be optimized during system manufacture to account for attenuation differences between parts and ensure that the signal transmitted to port I of a 99/1 coupler 131 is sufficient. This configuration defines a transmissive reference path, which has an advantage over Michelson interferometers in that the reference light is not returned back to the source 101.

A photodetector 132 in the interferometer monitors light coupled out of coupler 131. Alternatively, a monitoring detector could be positioned in the reference arm fiber 113. The photodetector 132 is used to measure the power of the source both for eye safety purposes and to monitor the degradation of the source.

Sample arm fiber 112 directs light into a delay line implemented using corner cube 124. The corner cube is translatable along an axis as indicated by arrows A to change the path length of the sample arm. The path length of the sample arm is adjusted with respect to the reference arm to select the depth in the tissue at which the OCT image will be centered. The light exiting the corner cube 124 is directed to a pair of scanning galvanometer minors 116 for scanning the beam in a plane perpendicular to the propagation axis of the beam. The light is then passed through a lens doublet defined by lens 150 and 152. A turning mirror 151 is interposed between the lenses. It is preferable that the spacing between lenses, and optical path length within lenses, along the OCT beam, such as between lenses 150 and 152, be greater than the free space OCT depth range so that reflections off the surfaces of the lenses will not create interference effects that might be interpreted as coming from structures in the eye.

The light beam is then turned towards the eye using a dichroic beam splitter 160. The dichroic beamsplitter 160 functions to directs light from the OCT path to the common optical path used by various subsystems and redirects OCT return light back along the OCT path while redirecting other light backscattered from the eye along a different path. The light is directed into the eye with a lens 162. Lens 162 is designed to correct for spherical aberrations in the eye. In order to compensate for refractive error, we adjust position of lens 162 with respect to the remainder of the optics. Light entering the eye is reflected back from various structures in the eye such as retinal layers. The reflected light travels back on the same path to input port III of coupler 111. Coupler 111 directs seventy percent of the light reflected from the source and returned to port II to the combining coupler 131 while thirty percent of the light returned from the source returns to the light source through port I. Alternatively, the 70/30 coupler 111 may be an 80/20 coupler or a 90/10 coupler.

Coupler 131 functions to combine light returning from the sample arm and arriving from the reference arm to create interference effects. A majority of this combined light is directed out of the coupler 131 at port III to a spectrometer 200. Further information about interferometer designs having a transmissive reference path can be found below in the section APPARATUS FOR OPTICAL COHERENCE TOMOGRAPHY.

A polarization paddle is provided to optimize signal strength. OCT depends on interference between sample and reference beams, and the interference of these beams produces a modulation in power to the extent that the polarizations of the beams match. Specifically, if one uses the common Poincaré sphere representation of polarizations, the amplitude of the interference fringes is proportional to the cosine of half the angle on the Poincaré sphere between the Poincaré sphere representations of the sample and reference polarizations.

Rotating birefringent elements are a common method of controlling polarization. In fiber optics, bending the fiber is a convenient means for creating birefringence, and rotating the orientation of the bends rotates the axis of birefringence. Such an assembly is often called a polarization paddle. (See, for example, chapter 9 of "Polarized Light in Fiber Optics" Edward Collett, (c) PolaWave Group Lincroft N.J. 2003.)

Perfect polarization matching requires three polarization paddles to compensate for arbitrary polarizations in the sample and reference arm. In practice, perfect polarization compensation is not required; only sufficient polarization alignment is necessary to enable detection of interference. A single paddle is sufficient to compensate for most polarization differences seen in practice so that detection loss is no more that 1-2 dB. The single paddle reduces equipment cost and simplifies the design and control and improves exam throughput efficiency.

Figure 4:
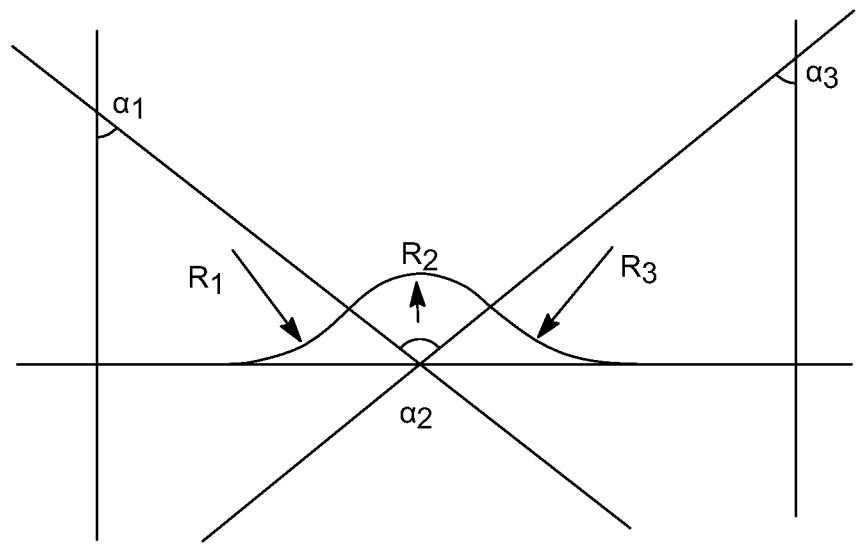
FIG. 4 is a polarization paddle design.

In the preferred embodiment, the single paddle is located in the sample arm but it could be located in the reference arm. A motor and hardware is included for a rotatable paddle to provide polarization compensation for the fiber. The fiber can be mounted with a U-shape bend onto the paddle as shown in FIG. 4, or in the more traditional circular loop. The paddle can rotate out of the plane of the paper with the U-shape remaining in one plane at all times. The design parameters are the three radii ($R_1$, $R_2$ and $R_3$) and the three angles ($\alpha_1$, $\alpha_2$, $\alpha_3$). These parameters are chosen to meet birefringence requirements as discussed below.

If the paddle is located in a single-pass portion of the interferometer, such as the reference path of a Mach-Zehnder design, then one expects theoretically that a quarter-wave paddle will be effective in matching polarizations. Suppose we are given two arbitrary polarizations and an adjustable quarter-wave plate affecting the first polarization. Imagine the locations A and B of the polarization states on the Poincaré sphere if we removed the quarter wave plate. The goal is to move A as close as possible to B by rotating A on the sphere by 90° about an equatorial axis of our choosing. Choose an axis x which puts both points in the hemisphere x>0. Sighting along the z axis, we can see both points on the same hemisphere, and want to move A by either +90° or −90°, whichever will bring A closer to B. This choice corresponds to choosing to place either the fast or slow axis of the wave plate in the direction corresponding to +x. It is always possible to move the first point so that it is (1) in the same x>0 hemisphere as the second point, and (2) within ±90° azimuthally about the z axis. The resulting distance between A and B is always less than 90°. The <90° result is best understood by visualization, but can also be proven using the law of cosines on the three directions A, B and x. The resulting fringe amplitude, then, is at least cosine 45° or 71% of what it would be with optimally matched polarization.

If the paddle is located substantially at the end of a bi-directional path, then two passes through a rotatable one-eighth wave paddle will have the same benefits as derived above for the single pass through a quarter-wave paddle. If the paddle is located in a bi-directional path but located such that the light experiences significant uncontrolled birefringence, such as by the sample, experimentation and simulation have shown that three-eights of a wave of birefringence more robustly restores the interference fringe amplitude.

The spectrometer 200 is of the type disclosed in U.S. patent Ser. No. 11/196,043, filed Aug. 3, 2005, (publication 2007/0030483) incorporated herein by reference. Briefly, the spectrometer is in a folded Littrow configuration. Light enters the spectrometer and is directed to a grating 230. Grating 230 is preferably blazed for 840 nm, with approximately 1200 lines/mm to give adequate spectral dispersion. Light reflected from grating 230 is directed to a pixel camera 250. The dispersion of the grating and the imaging lenses discussed below are chosen to spread wavelength from approximately 800 to 900 nm over the sensitive length of camera 250. A set of three lenses 240, 210 and 220 is located between the grating and the camera. The light passes through these three lenses both on the path to the grating and on the return path to the camera. While each of the lenses contributes to focusing and correction, lens 220 is the primary lens for focusing and collecting light from the grating. The grating is tilted in a way to induce conical diffraction which causes the returning light beam to be displaced away from the fiber input, slightly out of the plane of the figure, and towards the camera. The primary function of lens 210 is to correct for effects of conical diffraction. Lens 240 functions primarily as a field flattening lens.

The SD OCT system is capable of generating two- or three-dimensional images of the retina in a manner known in the prior art. The subject system has some additional capabilities that will be described below. However, one added feature is the ability to rapidly switch between imaging the retina to imaging of the cornea. This capability is provided by including an extra lens 180 which can be moved into the path of the light in the sample arm to permit focusing of the light onto the cornea. In conjunction with the movement of the lens 180 into position, the position of corner cube 124 is changed to allow the path length difference between the sample arm and reference arm to correspond to the position of the cornea. An advantage of this system is that the information about the cornea can be easily obtained without having to reposition the patient.

Figure 5:
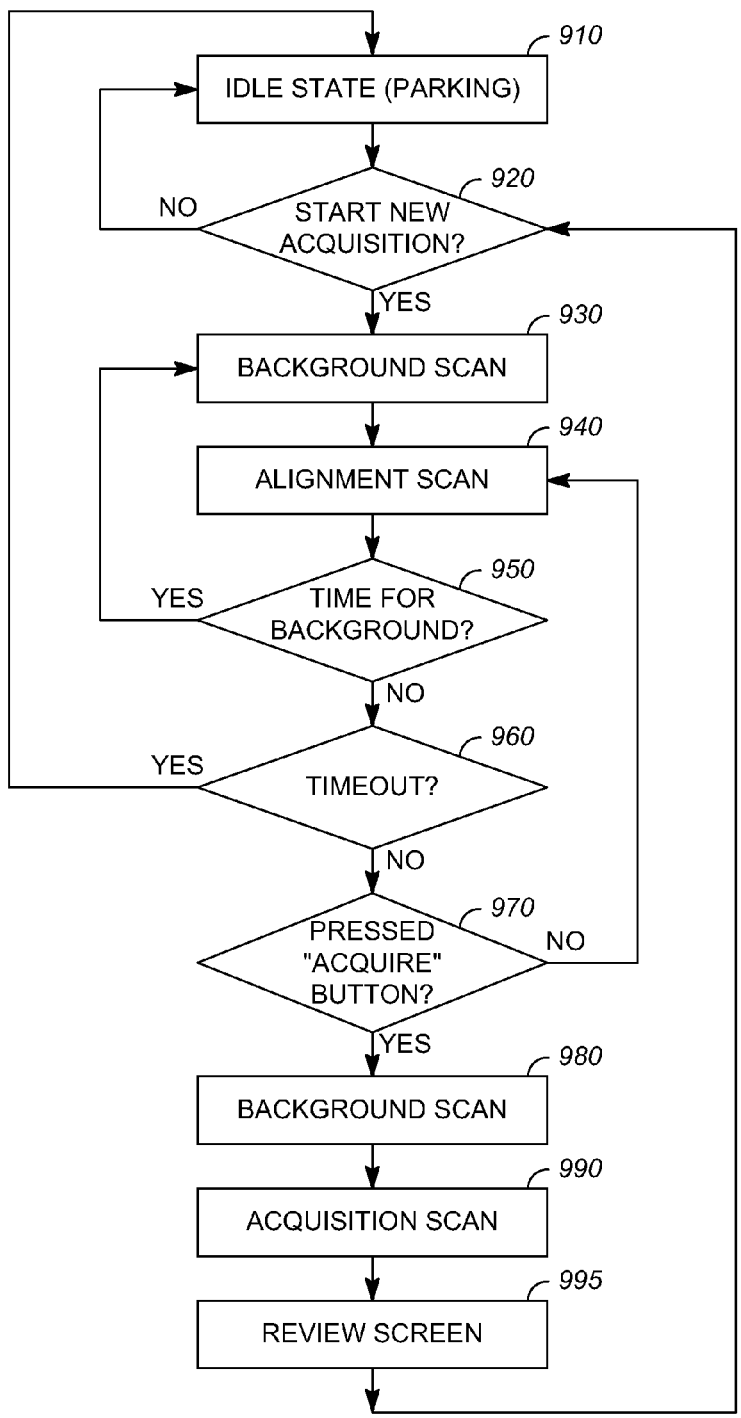
FIG. 5 is a flow chart of scan states during the operation of the instrument.

As an alternative to moving corner cube 124, mirrors can be moved to switch in and out an extra fold in the optical path length, as illustrated for example in FIG. 5 of U.S. patent application Ser. No. 11/243,665, filed Oct. 5, 2005, (publication 2007/0076217) incorporated herein by reference. Other alternatives to moving corner cube 124 are the rapid-scan optical delay (RSOD) devices disclosed in International Patent Application No. WO 2005/033624 and in U.S. Pat. No. 6,654,127, either of which can be configured to provide a change in group-delay, with relatively small phase delay. The small phase delay is advantageous here because changes in phase delay move the interference fringes across the camera 250, which reduces the fringe intensity if the fringes move during exposure of camera 250. The group-delay devices with small phase delay cause relatively less motion of the fringes the device is settling after a quick move.

While the optical delay does not need to be particularly rapid for centering the imaging region, the ability to change the optical delay rapidly is useful for adjusting the optical delay on a scan-by-scan basis. For example, an RSOD can be used to flatten the retina. Nominally, the retina will appear as a curved surface in a 3-D image of the eye. Using a predetermined delay profile, an RSOD can adjust the optical delay on each A-scan and flatten the curved surface. When sufficiently fast computation elements are available along with hardware feedback paths, on-the-fly optical delay adjustments can be computed from A-scan to A-scan. Alternatively, a sparse scan can obtain a select complement of A-scans which can be used to identify the retina in each A-scan and compute a fit to the retinal surface (say a spherical or parabolic fit), which can be used to generate a delay profile for the RSOD. Clearly, combinations of pre-determined profiles and on-the-fly computations can also be used to direct the RSOD to modify the optical delay on an A-scan by A-scan basis in a SD OCT system.

The second main sub-system is a fundus viewer. The preferred fundus viewer technology is the line scanning ophthalmoscope LSO 40. The LSO 40 includes a relatively narrow band light source which, in the preferred embodiment, is a super luminescent diode 410 emitting light at about 755 nm with bandwidth about 5 nm. The light source is polarized. Light from source 410 is passed through shaping optics 415 to create a line of light. The line of light is directed to a beam splitter 420 which redirects the light to scanning galvanometer mirror 430 for scanning the line in one axis perpendicular to the plane of propagation of the light. Beam splitter 420 comprises a reflective strip, so that illumination from source 410, focused to a line along this strip, is directed to the eye, while light returning from the eye largely passes around this strip toward imaging lens 480. The illuminating light is directed to a dichroic beam splitter 440 which is reflective of light at 755 nm and transmissive at shorter wavelengths. The light is passed through a lens doublet 450 to a dichroic beam splitter 460. Beam splitter 460 is reflective of light in the 700 nm wavelength region and transmissive for light at 755 nm and 550 nm wavelengths. Beam splitter 460 needs to have high transmissivity at 755 nm only for the polarization of light used in the LSO subsystem. The design of the dichroic coatings on beam splitter 460 is easier if only one polarization state needs to be optimized. (Analogous design optimization is available for beam splitters 460 and 160.) Light is then passed through beam splitter 160 into the eye. Beam splitter 160 is reflective of light over 800 nm and transmissive of light at shorter wavelengths. The beamsplitter 420 is nearly conjugate to the cornea, so that an image of the LSO light source reflected from the patient's cornea is formed on the reflective strip, thus blocking this corneal reflection from the imaging optics.

Light from the LSO 40 is reflected by the eye and returns on the same path to splitter 420. A portion of the reflected light is transmitted through splitter 420 and it is imaged via a lens 480 onto a line scan camera 490. Commercially available line scan cameras offering line rates around 10 kHz are appropriate for camera 490. As the galvanometer 430 is scanned, different portions of the retina are illuminated and imaged, so that a two-dimensional image of the patient's retina is built up from successive exposures of the camera. With 512 lines in a frame, a frame rate of 20 Hz is achieved. The scan range of galvanometer 430 is easily variable to adjust the field of view of the LSO.

The third main sub-system is an iris viewer 60. The iris viewer is used primarily to align the patient's eye with the optical axis of the device. The iris viewer includes an LED 610 positioned near lens 162 for illuminating the eye. Preferably, the LED generates light having a wavelength of about 700 nm. The reflected 700 nm light is captured by lens 162 and travels back through splitter 160 to splitter 460 where it is reflected back through a series of lenses to a CMOS camera 620. The LED can be polarized, or its output filtered by a polarizer, so that the light reflected from the iris is largely polarized, and beam splitter 460 optimized to reflect only one polarization state. Imaging the iris in polarized light has the side effect of revealing birefringence of the cornea. The camera 620 generates an output which is supplied to a monitor that will display an image of the iris. As discussed below, this image is used to position the patient.

The fourth main sub-system is a fixation system 50. Fixation system 50 includes a display pad 510 for generating fiducial marks that will be projected onto the patient's eye. The patient will be asked to fixate her eye on these fiducial marks. Pad 510 generates light at a visible wavelength preferably between 450 and 600 nm. The light from pad 510 is conditioned by lens system 520 and directed through dichroic beam splitters 440, 460 and 160 and focused into the eye via lens 162. The preferred fixation target is a variable sized, 2D fixation target. A 2D fixation target provides both a center fixation target and the ability to rapidly change visual stimuli for analysis of eye response. Preferably, the target size is variable from a point target to an oversized target embedded in a 120×120 pixel display covering a field of view of 30 degrees.

Figure 2:
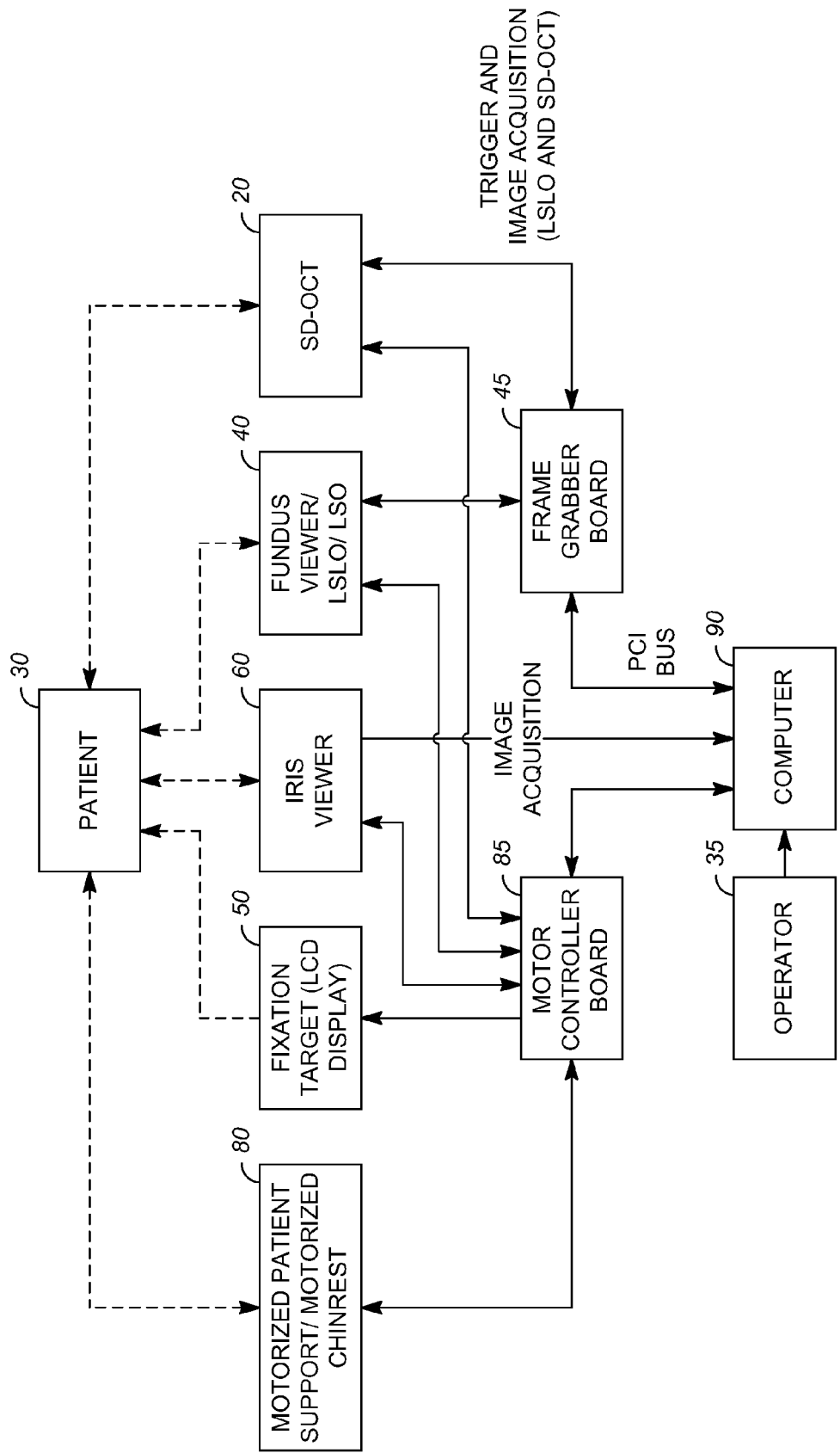
FIG. 2 is a system block diagram including the OCT system, the LSO system, the Fixation system, the Iris Viewer system, and the motorized chin rest.
Figure 3B:
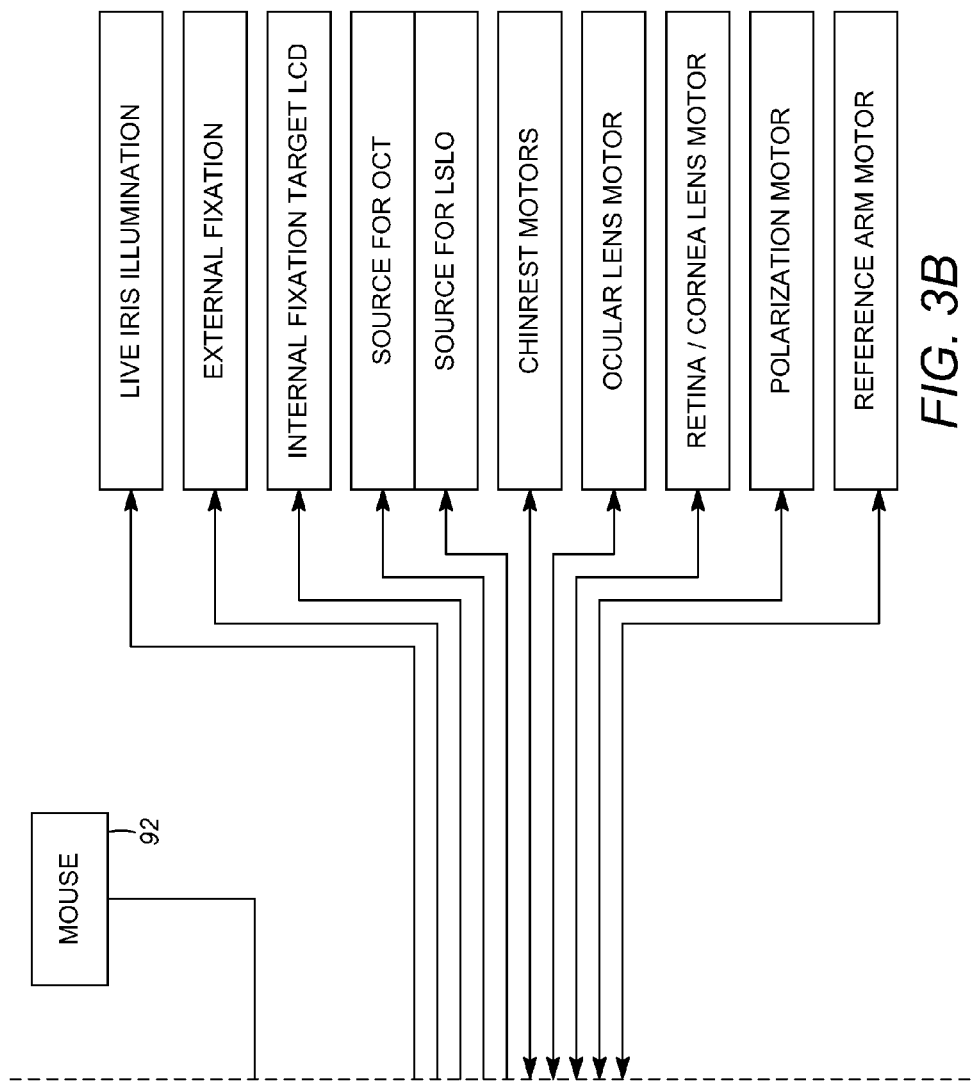

As shown in the system block diagram of FIG. 2, a host computer 90 is used to interface between the operator 35 and the integrated system to control the subsystems, either directly or through a controller such as a motor controller board 85, and to send and receive subsystem data, either directly or indirectly through and intermediary controller such as a frame grabber board 45. As shown in the electrical block diagram of FIG. 3, the host computer 90 provides the system with input devices (such as keyboard 91, mouse 92, or equivalents such as trackball or joystick) and output devices (such as monitors 93 and printers 94) as well as Input/Output devices such as digital storage devices such as hard drives (not shown), CDs (not shown), DVDs 95, etc., connection ports such as serial ports (not shown), parallel ports (not shown), USB ports 96, fire-wire ports (not shown), and the like, and network connections 97 to local, peer-to-peer, distributed, or even the world-wide web. The live iris camera 98 is preferably a direct PC peripheral, though it could also be integrated into the frame grabber, providing yet another image input to that device. The architecture of the frame grabber board can enable real time tracking by image processing an image on the host PC and updating the galvo X and Y offsets on the frame grabber in real time. In this embodiment, the galvo scan pattern is corrected and the appropriate region is imaged, even in the presence of eye motion.

In order to improve the functionality of the device, a specific effort was made to insure that the various sub-systems worked together in a cooperative manner. For example, the OCT, LSO and iris viewer are all telecentric systems, so that adjusting focus does not change the magnification of the image. The optical systems that focus on the retina, the LSO, OCT, and fixation, are parfocal so that they are simultaneously in focus on the retina after compensation for refractive error. The systems that focus on the retina use different wavelengths, so their focus adjustments are calibrated to compensate for the different focal lengths of the human eye at these various wavelengths. The systems that image the retina, OCT and LSO, are confocal systems, meaning that small areas of illumination are swept across the retina and images of these areas directed to matched sensitive areas on the detectors. Confocal imaging reduces glare from corneal reflections and scattering from other ocular media such as a cataract.

This design takes care to minimize polarization dependence in the optics along the OCT beam path. For example, differences in optical delay between the polarization states, known as polarization mode dispersion (PMD) cause OCT images with different depths for each polarization state. Given that the polarization state changes on transmission through the eye, polarization is difficult to fully control, and PMD generally leads to broadening of the axial (depth) resolution in the OCT image. The dichroic beam splitters along the OCT path reflect, as opposed to transmit, the OCT beam because the beam reflected from dichroic coatings typically has less PMD than the transmitted beam. Smaller polarization dependent effects, such as fractions of a wave of birefringence, are also controlled. The beam splitters are placed in locations where the OCT beam is telecentric, meaning the chief rays of the OCT beams for various positions of the scanner 116 are parallel, so that the angular-dependent polarization effects of the beam splitters do not change as the OCT beam is scanned.

In use, the first step is to align the patient with the device. In the preferred embodiment, the patient's head is put into a motorized headrest. A suitable headrest is described in U.S. patent application Ser. No. 10/843,767, filed May 12, 2004 (publication No. 2005/0254009) which is incorporated herein by reference. The doctor will ask the patient to view the fiducial marks generated by the pad 510. At the same time, the doctor will observe the eye via a display (not shown) associated with the camera 620 of the iris viewer. Initially, the distance between the patient's eye and the lens 162 is adjusted for best focus of the iris. Once the proper spacing has been achieved, the separation between the lens 162 and eye is held constant while the position of the eye with respect to the OCT system is varied to position the center of the OCT image at the desired depth within the eye. Lens 162 is not carried by the motorized chin support 80 (FIG. 2). Rather, a separate translation system is provided which is operatively linked to the motion of the chin support during this positioning step. Further information about the approach used to position and align the patient's eye can be found below in the section "METHOD OF PATIENT ALIGNMENT FOR MULTI-FUNCTIONAL FUNDUS IMAGING".

The primary purpose of the iris viewer is to help the operator center the patient's pupil so that the OCT and LSO beams pass through the pupil to the iris. A continuous view of the iris is helpful in keeping the patient's pupil centered during retinal imaging. Note that the iris viewer can also be used to help position the OCT beam around cataracts. Further, it can be used to help collect OCT images through different portions of the pupil, collecting light at different scattered angles from the retina.

Once the patient has been aligned, a wide variety of OCT images can be generated. The Fourier transform of the signals from the spectrometer provide A-scan information at each X and Y position of the beam. (In some methods scans are repeated at the same X and Y position to reveal time-dependent effects including pulsatile flow, Doppler shifts, etc.) This data can be collected and stored. Some A-scans can be acquired for purposes other than imaging. For example, the scanning system 116 can direct the OCT beam in a circle outside the aperture of lens 162, during which time the camera records the reference signal only, with no signal from the sample, thus collecting a background signal for use in processing. The processor can then generate and display other image information (such as B-scans, en face images, Doppler images, etc.) familiar to the doctor. In addition to some of the more conventional imaging modalities currently available on existing systems, the subject apparatus has been configured to provide additional functionality.

For example, the system is configured to generate fundus type images based on OCT data. This approach is described in U.S. patent application Ser. No. 11/219,992, filed Sep. 6, 2005 (publication 2006/0119858) and incorporated herein by reference. In this type of analysis, the intensity information over the depth range for the OCT data at any particular X/Y location is integrated to generate a pixel in the fundus image. The integration of intensity over a depth range to generate the fundus pixel may be performed by either accumulating intensities prior to compression (nominally logarithmic) for display or by compression of intensities prior to accumulation. The fundus image can be continuously displayed for the doctor to help interpret the OCT images and position the device. This fundus image based on OCT data is especially valuable for registration of the location of the underlying OCT cross-sections, to an en-face view of the retina.

The OCT may be used to generate maps with three-dimensional rendering of elevation, topographical maps or color or grayscale maps. U.S. patent application Ser. No. 11/717,263, Mar. 13, 2007, and incorporated by reference, discloses a variety of approaches including collecting compound OCT scans for high definition scans and a data cube to provide context for high definition scans. Also disclosed are standardization techniques for orientation, diagnostic metrics of texture and heterogeneity, retinal fluid maps, etc.

The section METHOD FOR COMBINING B-SCANS ("THICK B-SCAN"), below, discloses the concept of combining adjacent B-scans to reduce noise and speckle and give an enhanced visual impression.

The software can be set up to generate elevation maps of tissue with respect to fitted reference surfaces. This approach is described in U.S. patent application Ser. No. 11/223,549, filed Sep. 9, 2005 (publication 2007/0103693) and incorporated herein by reference.

The system may also be set up so that the chromatic dispersion of the sample and reference paths are different from each other to create a variation in the relative group delay as a function of optical frequency between the sample and reference paths. Thereafter, the measured interference spectrum can be multiplied by a complex phase factor to compensate for the mismatch. In this manner, the image contrast between reflections from the sample and image artifacts can be increased so that the doctor can better discern actual tissue images. Further information on this approach is set forth in U.S. patent application Ser. No. 11/334,964, filed Jan. 19, 2006, (publication 2006/0171503) incorporated herein by reference.

As noted above, one problem associated with prior art systems relates to errors resulting from the movement of the patient's eye during imaging. Errors of this type are reduced in the subject system because the scanning speed is much faster. For comparison, the time needed to scan the eye using our current Stratus system is on the order of 2 seconds, while the subject system can cover the same scan region in only 0.026 seconds.

The increase in speed is so great that new scanning sequences can directly collect 3-D imaging data without the need for intervening tomograms. In some cases, performing scanning sequences collecting data in 2-D planar tomograms and then building a 3-D volume from the 2-D slices is preferable because then existing software can be used for visualization, reducing costs and time-to-market. Nonetheless, direct collection of 3-D voxel data in real-time using spectral domain optical coherence systems is now possible and the 3-D volume can be rendered directly for display.

In addition to increasing the scanning speed, other approaches have been developed to still further reduce problems associated with eye movement during measurement. For example, U.S. patent application Ser. No. 11/331,567, filed Jan. 13, 2006 (publication No. 2006/0164653) and incorporated herein by reference discloses the concept of taking a few partial, fast OCT scans and using this information to provide registration information during the slower, more complete OCT scans. In another approach, the LSO system 40 can be used to generate guideposts that can then be compared in the processor to the OCT images. The information can be used to control the scanning of the galvanometer minors 116 in real time to compensate for patient eye movement. Alternatively, the LSO data can be used in post-processing to properly register the data acquired from the OCT system. More information about this approach can be found in U.S. patent application Ser. No. 11/389,351, filed Mar. 24, 2006 (publication 2006/0228011) and incorporated herein by reference.

Figure 6:
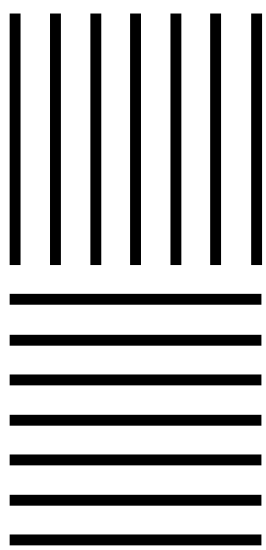
FIG. 6 is an example internal test target.

It is also desired that the device exhibit long term repeatability and stability in the field. In the past, external targets where used by the doctor to facilitate alignment and calibration. The subject system has been provided with an internal calibration system to simplify the process of making sure the OCT and LSO systems are coaxially aligned. More specifically, a target 710 is provided which preferably includes fiducial marks such as crosshairs or horizontal and vertical alignment bars (see FIG. 6). An auxiliary mirror 720 is provided located just beyond the zone where the OCT and LSO beams are scanned when measuring the patient. During a calibration step, the galvanometer mirrors 116 and 430 are positioned so that the light from the OCT and LSO systems strike minor 720 and are directed to target 710. The reflected light is imaged by the two respective detection systems. The driving systems for minors 116 and 430 are adjusted until the images overlap. Information defining the position of the galvanometer mirrors is stored and used to calibrate the device (see FIG. 7). The crosshairs in target 710 can be grooves to facilitate imaging by the OCT device. Target 710 preferably includes reflectors at various depths for calibration of axial length measurements by OCT and confirmation of the axial resolution of the OCT system.

Yet another use for internal calibration is a galvanometer test. After scanning many times (up to billions of cycles), the motors of optical scanning galvanometers mechanically wear. Before catastrophic failure, their bearings and lubricants deteriorate and affect performance. These motors are typically driven by servo amplifiers that attempt to minimize the difference between the actual galvanometer motor position and a commanded position. The actual position is provided either as an analog or digital signal. In ophthalmic scanning, image quality and repeatability is directly dependent on galvanometer performance, so it is important to be able to characterize the closed loop response and adapt performance to achieve the desired response. The desired position may be achieved by adapting the loop filter of the servo or the command signal. In cases where there is no adequate internal alternative available to achieve the required performance, the system can issue a request service. The service request may be either through a notice to the user on the system or a notice across a network to either administrative personnel or directly to the service organization.

This internal calibration may be performed on an internal schedule, such as monthly or weekly or on every n-th boot (where n is a positive integer), or through remote service and diagnostics.

The arrangement of the sub-systems leads to some novel combination. For example, and as noted above, the OCT system, LSO, iris viewer and fixation system are all parfocal. The iris viewer, which preferably displays a continuous image of the iris, greatly facilitates the alignment of the OCT system measurement system. This approach can be compared to the prior art approach, often used in fundus camera, of using the retinal imaging system, here an LSO, to first image the iris at a distance spaced significantly from the optimal positioning necessary to obtain an OCT image. In order to then position the device to obtain a OCT and LSO images of the retina, the doctor would have to carefully move the patient and imaging system closer together, along a line without deviation so that the imaging paths remain centered on the pupil. This adjustment would be difficult because the doctor would no longer have the image of the iris displayed.

FIG. 2 is a block diagram of the overall system. It shows the operator 35 interacts with the computer 90. The computer 90 acquires Iris Viewer image data directly from the Iris Viewer 60 while fundus and OCT image information are received through the frame grabber board 45. Alternatively, in some instances, one or more high performance graphics boards can substitute for the frame grabber board 45 however, because of the multiple sources of image frames, specialized hardware was preferable for the preferred design. The controller board 85 performs the real-time system control for the OCT system 20, the fundus viewer 40, the fixation target 50, the iris viewer 60, and the motorized chin rest 80.

FIG. 5 is a flow chart of one embodiment of the OCT scan states during operation of the instrument. The OCT system remains is a system idle state until the operator indicates the start of a new acquisition 920. Since this chart is concerned with the scan states of the OCT system, the flow in this chart assumes that the iris image is already in focus. Then the first task is to align the scan. First we perform a background scan 930 to determine current scan position. The scan is then aligned 940 by setting the OCT reference depth using the Z-motor and moving the combined ocular lens and eye with synchronized x-, y-, and z-motion (using the chinrest and Z-motor in combination) to optimize the focus of the fundus image. The system process 950 intermittently returns the OCT system to the background scan state 940 to ensure that the alignment scan state 940 is performed using correct background information. The system remains in the alignment scan state until the operator starts the acquisition state 970, unless returned to a background scan state or a system timeout 960 occurs. The system timeout state 960 is entered after a fixed interval in which the operator has not determined to acquire data. In this embodiment, once the operator decides to acquire data, first a background scan is performed 980 and the acquisition scan is performed 990. On acquisition scan completion, the system enters a review data state 995 and the operator can review the acquired data through various image display and analysis tools. On completion of the data review, the system is returned to the system idle state 910.

Apparatus for Optical Coherence Tomography

The following embodiments describe interferometers for use in the invention of record. Coherence-domain imaging techniques such as OCT preferably use light sources with short axial coherence length, but with spatial coherence in the transverse directions. Superluminescent diodes, which are similar in structure to diode lasers, have short temporal coherence and broad spatial coherence. By design, they do not laser because there is insufficient optical feedback. Superluminescent diodes are typically sensitive to optical back-reflection of output light potentially causing output power fluctuations and shortened lifetime.

The most common interferometer configuration for OCT is the Michelson interferometer. Most Michelson interferometers return some reference arm light to the source. The light returning to the source can be diverted by the use of non-reciprocal optical elements. To avoid the expense of non-reciprocal optical elements, one can control the polarization state of the light and divert light returning to the source based on its polarization state.

Some interferometer topologies allow the reference path to be completely in fiber, allowing simple construction. Other interferometers using essentially the same topology allow the reference path to be nearly completely in fiber, only deviating from continuous fiber to insert simple free-space optics, such as a leakage optical attenuator. In OCT, the optical group delays must be approximately matched between sample and reference paths. This matching is typically accomplished by adjusting the reference optical path length. If the reference path is completely in fiber then the sample path length can be varied instead, as noted in U.S. Pat. No. 5,321,501, c. 12, 11.16-21.

The OCT apparatus disclosed herein efficiently collects light from the eye, uses a reflective sample path, returns no reference light to the source, and does not require circulators or other non-reciprocal elements.

Extreme split ratios in the fiber couplers can be avoided and one configuration allows a safety monitor tap close to the sample arm tap.

FIG. 8 illustrates the topology of an interferometer for OCT that reduces reflections of the light back into the source. Low coherence light source 101 is typically a superluminescent diode (SLD) which typically tolerates back reflection of less that $10^{-3}$ of its output light. The SLD is coupled to source fiber 110 that routes light to directional coupler 111a. The optimal directional strength of the coupling depends on system design choices and may be 90/10 (as shown in FIG. 8) or 70/30 (as shown in FIG. 1) or other as availability permits. Directional coupler 111a splits the light into sample fiber 112a and reference fiber 113a. The sample path includes delay apparatus 114 to adjust the length of the sample path; shown in more detail in FIG. 9. The delay apparatus couples the light from fiber 112a to a free-space OCT beam 115. Transverse scanner 116 deflects the OCT beam and preferably creates a focus in the beam near the region of interest in sample 30a.

Some light scattered from sample 30a returns through the scanner and delay apparatus to sample fiber 112a. Coupler 111a routes this light through loop 117a to fiber coupler 131a, where it is interfered with the reference light. The combining coupler 131a provides two outputs. These outputs could be used for balanced detection (U.S. Pat. No. 5,321,501 FIG. 10) in which both detector 200 and detector 142c are used to collect light for OCT. Alternatively, the coupling ratio of coupler 131a can be adjusted to send most of the interfered light to a single OCT detector 200. Each OCT detector can be a single photodetector for use in time-domain OCT or swept-source OCT, or a spectrometer for use in spectral domain OCT.

Optional tap 121 diverts a fraction of the reference light to detector 122, which may be used to monitor the source power. (Some reasons for monitoring include safety of the sample and detection of degradation in the source 101.) The tap removes some fraction of optical power from the reference fiber 113a, reducing the power that reaches coupler 131a. Sensitivity in OCT can reach the shot-noise limit if the reference power is large enough to bring the interference signal above receiver noise, but not so large as to bring intensity noise or beat noise above the level of shot noise. The reference power is approximately determined by the source power, and the coupling ratios in directional couplers 111a and 131a, and adjusted by choice of tap 121.

The coupling ratios in directional couplers 111a, 131a and 121 are chosen to set a safe level of illumination to the sample, and to set the appropriate reference power at the detector or detectors. For example, in the case of ophthalmic OCT of the retina using light with wavelengths near 850 nm, the safe exposure level is approximately 0.5 mW, and the optimum reference level at the detector is approximately 0.005 mW. Sources are available in this wavelength range having output power of approximately 5 mW. For these conditions one would use a coupling ratio near 90%/10% in the splitting coupler 111a so that 10% of the source power reaches the sample. 90% of the scattered light will then be routed to loop 117a. In the case where there is a single OCT detector 200, the combining coupler 131a preferably routes most of the sample light to that detector. The splitting coupler routes 90% of source light, 4.5 mW, to reference fiber 113a, while only 0.005 mW is required at the detector. One could use a combining coupler 131a that couples 0.1% of the reference light into the single OCT detector 200, but in manufacture it is difficult to control the 0.1% coupling factor. A preferred solution is to use a 99%/1% split ratio in combining coupler 131a, and take advantage of the additional degree of freedom in tap 121 to adjust the reference power. Nominally, tapping 89% of the power form reference fiber 113a will provide an appropriate reference level of 0.005 mW at OCT detector 200, in this example.

As an alternative to adjusting the tap ratio of optional tap 121, one can adjust the reference level by including attenuating fiber (U.S. Pat. No. 5,633,974) in the reference path.

FIG. 9 illustrates one of several other possible interferometer topologies. Low coherence light from source 101 is divided by coupler 111b between fiber 112b and reference fiber 113b. Sample-routing coupler 141 further splits the light from fiber 112b between monitor 142 and sample fiber 112c. Light in sample fiber 112c is delayed by apparatus 114 and scanned by scanner 116 across sample 30b, and some light scattered from the sample is returned through these devices to sample fiber 112c. Some of the returned light, preferably a large fraction, is routed by sample-routing coupler 141 to combining coupler 131b, where it is interfered with the reference light. Again, one or both of the two outputs of combining coupler 131b can be used to detect the signal for OCT.

Considering an example as for FIG. 9, with a 5 mW source, the appropriate sample power can be achieved if splitting coupler 111b directs 90% of the source light to fiber 112b and 10% to the reference path, and sample-routing coupler 141 couples 12% of the light in fiber 112b to the sample fiber 112c. This split ratio in coupler 141 routes 88% of the light returned from the sample from fiber 112c to fiber 117b and toward the detector. The appropriate reference level is obtained if the combining coupler 131b couples 1% of the power in the reference fiber to the detector, allowing 99% of the light in fiber 117b to reach detector 200.

Preferably, the path length to the sample is changed while maintaining the OCT beam focus and without changing the range of sample to be scanned. One practical solution in ophthalmic imaging is placement of the path length adjustment between the output of the interferometer and the scanner. However, adjusting the path length can cause the OCT beam to move transversely, offsetting it from the center of the entrance aperture to the scanner. In typical scanners, this offset causes a phase shift in the OCT beam as the beam is scanned. Such phase shifts cause signal loss or positioning artifacts in frequency-domain techniques of OCT.

Figure 10A:
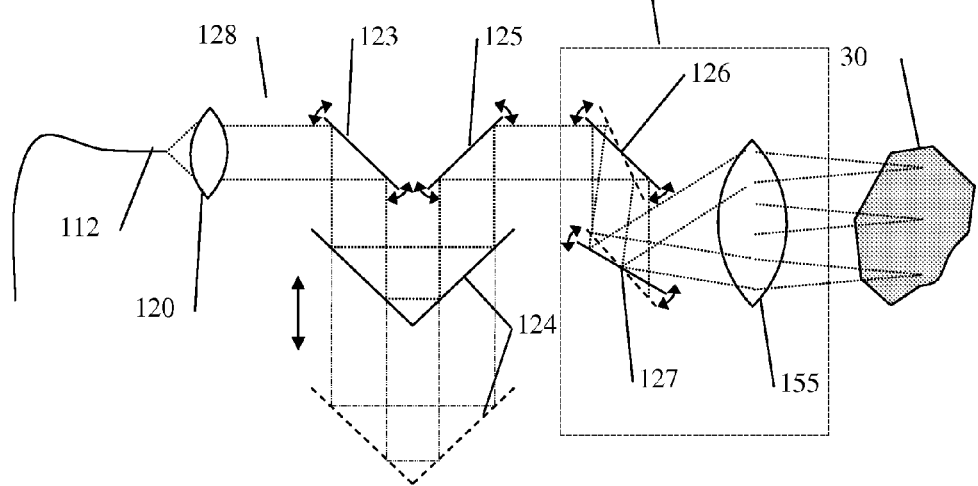
FIG. 10a illustrates the delay line alignment.

FIG. 10a illustrates the delay stage. Light from sample fiber 112 is collimated by lens 120 to form OCT beam 128. Alignment mirror 123 is one way to align the direction OCT beam 128 to be parallel to the travel of the moveable corner cube 124; the importance of this alignment is discussed later. Alternatively, beam 128 can be aligned by mechanically moving lens 120 in conjunction with the light emitting end of sample fiber 112. A moveable corner cube is one way to vary the optical path length of the OCT beam, in order to approximately match the optical group delays between the sample path and reference path.

Adjustment minor 125 directs the OCT beam to scanner 116. The scanner 116 can be implemented using a pair of rotatable mirrors 126 and 127, which in conjunction with scan lens 155 scan the OCT beam across sample 30.

If the OCT beam is not centered on the axis of rotation of scan minors 126 and 127, then as these mirrors rotate the optical path length to the sample is changed, as explained for example by Podoleanu (Podoleanu, A. G., G. M. Dobre, et al. "En-face coherence imaging using galvanometer scanner modulation." Optics Letters 23(3): 147-149 (1998)). The effect of the scanner on the sample path length is doubled because the return path of light scattered from the sample back to fiber 112 is also affected. This change in optical path length causes a phase shift in the interferogram. A continuous phase shift corresponds to a shift in optical frequency, and such a frequency shift due to relative motion is generally termed a Doppler shift. This Doppler shift has undesirable effects on the data collection by frequency-domain OCT techniques, as explained by Yun et al. (Yun, S. H., G. J. Tearney, et al. "Motion artifacts in optical coherence tomography with frequency-domain ranging." Optics Express 12(13): 2977-2998 (2004)).

Adjusting mirror 125 can be tipped and tilted to center the OCT beam on the axis of rotation of mirrors 126 and 127. The Doppler shift due to scanning can be easily be measured by the OCT system, so as to provide a Doppler signal to be nulled by adjustment of minor 125. One way to measure this signal is to provide a non-moving sample 30, repeatedly scan the OCT beam across the sample, and record closely-spaced OCT interferograms. Pairs of neighboring interferograms should be recorded from locations of tissue that are close compared with the optical resolution of the scanner, so the sampled regions significantly overlap. Pairs of neighboring interferograms differ largely in the phase shift caused by the optical path length change associated with transverse scanning. The phase shift between neighboring interferograms is thus a measure of the phase shift associated with the scanner, and provides a signal which is zero when the OCT beam is properly centered. Scanning the beam in alternate directions produces an alternating phase shift associated with the scanner, allowing one to distinguish this phase shift from other effects, such as the Doppler shift due to unintentional motion of the sample. Scanning each of minor 127 and 126 separately produces a phase shift proportional to the misalignment of the OCT beam off the respective axes of rotations of these mirrors.

If the center of the beam is mis-positioned by as little as 0.5 mm, then the phase shift induced by rotation of the galvo is significant. The galvo rotates 0.7 degrees mechanical per millisecond during a 20-degree cube. The motion of the mirror at the beam center is 6 mm/s, moving 240 nm during a 40 µs exposure. This motion is sufficient to cause significant fringe washout. The misalignment tolerance follows from the acceptable sensitivity loss due to fringe washout. The sensitivity loss due to axial motion can be found from Yun et al [Optics Express 12(13): 2977-2998 (2004)] and in terms of decibels the loss in sensitivity is $$2.9 \text{ dB}(q\Delta z)^2 = 18 \text{ dB}(\Delta z/\lambda)^2.$$

Requiring the axial sensitivity loss to be less than 0.5 dB yields that the $\Delta z$ due to minor misalignment should be less than $0.167 * \lambda = 0.14$ µm for $\lambda = f$ nm. During the exposure of one A-scan from in a 128×128 cube covering 20°, we move the beam 0.16° in the patient's field of view. For a typical optical setup, the pupil will be imaged on the scanning mirrors, but with magnification typically 2.5, so that the minors need rotate only 1/5 of the angular sweep of the beam at the patient's pupil. Thus, the scan minor rotates by 0.03° during the exposure of one A-scan. The resulting misalignment tolerance is then $$0.14 \text{ µm}/[2 \tan(0.03°)] \approx 135 \text{ µm}.$$

Note that the tolerance to lateral misalignment, between the OCT beam and the rotation axes of the scanners, scales with the size of the image of the pupil on the scanner.

In some applications, there is a fast scan direction and a slow scan direction. For example, minor 127 may scan rows across sample 320 and mirror 126 may move less often to move the OCT beam between scan rows. In these situations one degree of freedom is relatively more important in the adjustment of minor 125. In general there is one direction of scan that is relatively faster than another, and in general there is one direction for which stable alignment is relatively more difficult. The design will preferably choose the more stable alignment direction to be the direction associated with phase shifts due to the faster direction of scan.

The measured phase shifts associated with scanning each mirror 126 and 127 can provide feedback to drive adjusting minor 125 to the position that gives a null phase shift. Such a feedback system would allow the apparatus to self align during operation, if the subjects are relatively still.

Alternatively to feedback using OCT, the correct position of the OCT beam can be marked by other means. For example, a beam splitter can direct a small fraction of light from OCT beam 128 to a position-sensitive detector that is preferably close to the location conjugate to the rotation axes of minors 126 and 127. The proper position of the OCT beam is associated with the signal values output from this position-sensitive detector during a condition of correct adjustment. In operation, the system can adjust mirror 125 to restore the signal from the position-sensitive detectors that corresponds to correct adjustment of the OCT beam position.

Figure 10B:
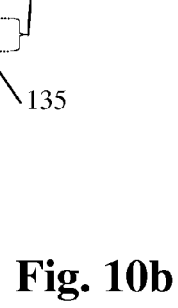
FIG. 10b illustrates a consequence of delay line misalignment.

The correct adjustment of the OCT beam on the scanner can be adversely affected by motion of the delay stage 114. If the OCT beam 128 is not aimed to be parallel to the direction of motion of corner cube 124, then the transverse position of the retro-reflected beam will change upon translation of the corner cube. FIG. 10a illustrates two positions of the corner cube 124 and the respective positions of the retro-reflected OCT beam. In FIG. 10a, the drift in adjustment has been corrected using the feedback mechanisms discussed previously so that the beam position out of the corner cube after translation of the corner cube coincides with the position of the beam out of the corner cube before translation. FIG. 10b illustrates two positions of the corner cube 124 and the respective positions of the retro-reflected OCT beam. Beam 133 is the retro-reflected OCT beam directed to scanning mirrors 126 and 127 before translation of corner cube 124, while beam 135 is the retro-reflected OCT beam directed to scanning minors 126 and 127 after translation of corner cube 124. It is illustrated here that the beam out of the corner cube is not only delayed, but it is also translated unless the entrance beam is properly aligned.

Feedback correction of the adjustment minor 125 will be easier, and possibly un-necessary, if the OCT beam is well aligned to the direction of travel of delay stage 114. Such alignment can be implemented by appropriate tip and tilt of alignment mirror 123. One method for alignment of minor 123 is an extension of the method used to adjust mirror 125. The phase shift associated with scanning (or the position of the OCT beam on a position-sensitive detector) can be measured for two locations of corner cube 124. Minor 123 is aligned null any change in phase shift (or position-sensor signal) with motion of the corner cube 124.

The delay rail that moves cube 124 is preferably mounted in an effectively kinematic way, to avoid misalignments of the OCT beam caused by strains in the optical mounts, such as those caused by thermal expansion. For example, FIG. 11 shows such a rail 171 mounted to plate 172 via bolts 175 and 176. If the bolt holes in plate 172 become improperly spaced due to thermal expansion of plate 172, then rail 171 could become bent out of plane of the figure; and the OCT beam could be shifted transversely from its desired location. Cutting holes 191 and 192 into plate 172 allows the remaining plate material in 193 to flex, so that the bolts 175 and 176 can maintain the proper spacing to match their holes in rail 171, and so that rail 171 remains straight. The mounting is effectively kinematic because it effectively relaxes the axial (z-axis in the figure) constraint on the position of rail 171. Without holes 191 and 192, bolts 175 and 176 imposed competing constraints on the axial position of the rail; the flexibility of material 193 relieves the redundant constraint.

Alternatives to expansion holes include: applying a heat sink to the support plate 172 or manufacturing the system so that excess heat does not accumulate at plate 172. Alternatively, plate 172 can be manufactured from materials with sufficient strength to support the rail, but a low enough expansion coefficient to prevent unacceptable flexing of the rail 171. Alternatively, combinations of these mechanisms or others can be used to ensure proper alignment of the corner cube 124 during system operation.

Corner cube 124 is often constructed from solid glass, using internal reflections to guide the beam. The remaining surface of the corner cube can produce weaker reflections. Such reflections are undesirable in an OCT system because if they either return to the fiber 112, or follow paths parallel to the main OCT beam, they can produce additional interference signals corresponding to different optical delays from that of the main beam. The additional interference signals can result in ghost images. If a corner cube is used in the longitudinal delay device, intentional misalignment or anti-reflection coating can be used to reduce reflections.

The OCT interferometer of FIG. 8 has its reference path entirely in fiber, while the sample path contains some air. (Air space is required for example in delay line, scan optics and working distance from optics to the sample). The different chromatic dispersions of fiber and air cause the relative optical delay between reference path and sample path to vary across optical frequency (see, for example, co-pending U.S. patent Ser. No. 11/334,964, filed Jan. 19, 2006, publication 2006/0171503, incorporated herein by reference). This variation in optical delay, if not corrected, leads to an uncertainty in the optical path length to each scattering center in the sample, worsening the axial resolution of the resulting tomograms. At certain wavelengths, such as near 1300 nm, the chromatic dispersion of fiber is near zero, so an interferometer configuration in FIG. 1 requires no correction for mismatched dispersion. For many applications of OCT different wavelengths are preferred, such as retinal OCT in which absorption by water in the eye would absorbs 95% of 1300 nm scattered from the retina, before that light exits through the front of the eye.

In order to manage the mismatch in chromatic dispersion, some elements in the sample path, which tends to have lower dispersion than the all fiber reference path, can be constructed using highly-dispersive glasses. For example, flint glass has significantly greater chromatic dispersion than optical fiber, so constructing corner cube 124 from flint glass significantly reduces the mismatch in chromatic dispersion. Each 1 mm of flint glass substituting for crown glass in the sample path approximately balances the chromatic dispersion mismatch resulting form the inclusion of 6 mm air in the sample path. Substituting sufficient flint glass for crown glass can also overcompensate, and reverse the sign of dispersion mismatch, if desired.

Previous OCT devices required balanced chromatic dispersion between sample and reference paths. If the reference path is entirely, or nearly entirely, in fiber and some of the sample path is in air, there is typically a mismatch in chromatic dispersion. Such devices perform best when using wavelengths for which the chromatic dispersion of the optical fiber is nearly zero. This restriction limits the device applications to those where the operation wavelength is chosen based on chromatic dispersion properties and not based on subject penetration or image optimization. Optical devices can be built to compensate for dispersion but often at the cost of optical loss, so these devices in the sample path would typically reduce sensitivity. Alternatively, one can numerically compensate the chromatic dispersion mismatch. Numerical compensation has benefits as described in the above cited U.S. Patent Publication No. 2006/0171503. These benefits work best when the physical dispersion mismatch is within bounds, so, so even with numerical compensation some method of controlling the dispersion is desired.

Having the reference path entirely or primarily in fiber does increase the opportunity for polarization mode dispersion (PMD) in the fiber (Raja) which causes an undesirably variability in optical path length with respect to the polarization state. When building any fiber interferometer one often has to make splices, which can fail, and to make the lengths of the fibers correct to match the optical path length of the reference and sample arms. Therefore one wants to be able to re-cut and re-splice the fiber. This is typically facilitated by placing extra loops in each of the sample and reference arms, with one loop from each arm removed each time the fiber is re-cut and re-splice. Therefore, one wants to have a considerable number of fiber loops. This leads to additional length of fiber and the potential for considerable PMD. The desire to fit the fibers in a small space increases the polarization mode dispersion, because bending induced polarization mode dispersion increases with smaller bend radius.

PMD can be reduced by careful routing of the fiber; for example, the PMD caused by bends in a horizontal plane can be compensated by following the horizontal bend with a vertical bend that provides approximately the opposite PMD. Such local compensation has the advantage that the net birefringence change is zero when a loop is removed, as for re-splicing of the fiber. Another advantage is that the compensating birefringence has the same temperature-dependence as the birefringence to be compensated, as they arise from the same physical cause. FIG. 12 illustrates one way to achieve these compensating bends 144. Each pass of fiber through the configuration drawn approximately compensates the birefringence in a larger fiber loop (not shown) having a total bend of 360-degrees with bend sections having 24 mm bend radius. The 201-degree bends of radius 14 mm fiber-bend in an orthogonal plane have approximately equal-magnitude birefringence of opposite sign.

In summary, the interferometer configurations of FIGS. 8-12 and their equivalents, make efficient use of light returned from the eye, compared to a Michelson interferometer. Such configurations enable setting appropriate reference signal levels at the detector. By using a variable delay in the sample arm, no reference arm reflector is required, which reduces the number of fiber-couplings and avoids delay-dependent variations in the reference arm signal level. No fiber moves or bends with this configuration. Although various embodiments that incorporate the teachings of the present invention have been shown and described in detail herein, those skilled in the art can readily devise many other varied embodiments that still incorporate these teachings.

Method of Patient Alignment for Multifunctional Fundus Imaging

Figure 13:
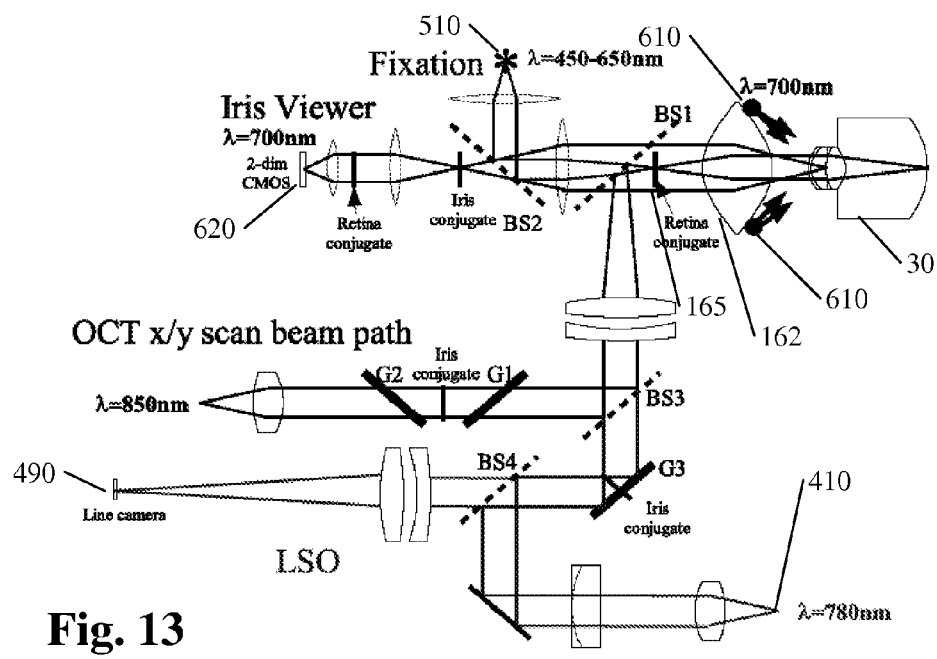
FIG. 13 illustrates a system with a large number of optical components working off the left side of a retinal conjugate, with the ocular lens and eye on the right hand side of the retinal conjugate.

The following embodiment included in one variation of the present invention describes a method of patient alignment for fundus imaging. This embodiment uses a suitable headrest, like the one described in U.S. patent application Ser. No. 10/843,767, filed May 12, 2004 (publication 2005/0254009) which is incorporated herein by reference. In this method, whose optical paths are shown in FIG. 13, one moves the patient head relative to an ocular lens 162 to set the human pupil at the entrance pupil of the instrument, then moves the ocular lens and patient head together to correct for refractive error. In FIG. 13, the vertical line 165 left of the eye and ocular lens indicates the position of the retinal image formed by the ocular lens; this line is the retinal conjugate. The figure illustrates a system with a large number of optical components to the left of a retinal conjugate, with the ocular lens and eye to the right of the retinal conjugate. In the description below, the terms headrest and chinrest are used interchangeably, referring to a suitable headrest as described in U.S. Patent Publication 2005/0254009 capable of head support and functionality that moves the patient's eye 30 at least along the optical axis, denoted as the z axis.

The chief ray of the scanning OCT beam and the rays of light used in the fundus imager both form ray pencils with a vertex at the center of the entrance pupil of the instrument. The scanning galvanometers in an OCT scanner or scanning ophthalmoscope determine the location of the vertex of the set of chief rays in the scanning beam. To get the beams into the eye the entrance pupil of the instrument must overlap the pupil of the eye.

It is advantageous to simultaneously maintain a focused image of the pupil of the eye for guidance in positioning of the eye so that the OCT and fundus microscope optical paths pass through the pupil of the eye.

The refractive error of the human eye varies over a range of approximately ±20 diopters. Therefore, there is a need to focus any OCT sample beam and the imaging optics of a fundus microscope to compensate for the refractive error of the human eye.

While making these two adjustments, it is advantageous to keep the working distance small (for better field of view without excessive size of optics) but yet large enough for patient safety. This leads to designs where the entrance pupil is at a fixed, safe, distance from the closest lens to the patient.

The Visucam non-mydriatic fundus camera, uses a separate off-axis iris view for alignment. The two adjustments are 1) camera-to-patient distance to set the working distance, guided by the iris camera and 2) refractive correction by moving a lens within the camera.

Use of an ocular lens with a slit-lamp comprises moving the biomicroscope portion of the slit lamp to focus on the retinal image formed by the hand-held ocular lens.

Fundus cameras typically move an internal lens for compensation of refractive error. Typically a retinal conjugate is formed in the instrument, at a location depending on the patent's refractive error; at this location the pupil of the eye is typically imaged at infinity. A moveable lens within the instrument is moved to focus on this retinal conjugate. The pupil of the eye is typically imaged at the back focal plane of this imaging lens.

U.S. Pat. No. 5,537,162 describes how to move the beam scanning mechanism with the moveable lens, so as to keep the vertex of bundle of chief rays of the scanning beam at the back focal plane of the moving lens.

Rather than move the moveable lens and beam scanner, we move the ocular lens and the patient together so that the retinal conjugate is formed at a standard location with respect to the remainder of the optics of the instrument.

An alternative solution would be to use a variable-power 1:1 relay system to re-form the retinal conjugate at a standard location. Another alternative is to use moveable minors to fold the optical path (in the shape of a trombone, for example) and extend the optical distance using the moveable minors so as to bring the retinal conjugate to a standard location.

The configurations described here have the advantage that the angular magnification, from the human pupil to the scanning mirrors, remains nearly constant in the face of compensation for refractive error. This feature means allows the scan range of the OCT beam, in terms of angle in the visual field, to be determined based on the turning angles scanning mirrors, without need for correction based on the motion of lenses for refractive error compensation.

Figure 14A:
FIG. 14a is a table of steps used for alignment of an OCT imaging system.

FIGS. 14a and 14b provide a table listing the alignment steps for imaging, 14b providing optional steps. Experience has shown that all these steps can be conducted pretty much in any order, with the exception that the working distance has to be set first. Otherwise, the adjustments can be performed in any order.

All motor positions (chinrest x, y, z, ocular, polarization, z-motor) can be recorded for every patient and restored upon repeat visits.

The preferred optical coherence tomography device will contain a feature called "pupil following". This is not pupil tracking, but rather a mechanism that moves the head (and therefore the pupil) when the fixation target is moved.

When we move the fixation target in the optical coherence tomography device, the patient rotates their eye to follow the fixation target. While they do so, their pupil shifts because the center of rotation is behind the pupil. Therefore the chinrest has to be moved sideways in order to compensate for this.

The current implementation does the following:
1. It moves the fixation target continuously (rather than in one large step where the fixation target suddenly is located somewhere else and the patient has to search)
2. It compensates pupil shift based on a simplified eye model and rotation.

For a "nominal" patient's eye the operator would never see the pupil move at all. For a real patient there is some adjustment necessary, but it helps.

Additionally, a corneal scan can be performed. One can insert a flip-in diverging lens 180 (FIG. 1) after the galvanometers, so as to form a virtual point source near the pupil conjugate. This results in a beam waist near the pupil of the subject. One can set the power of the lens so that the beam waist is on the cornea of a typical eye, and move the z-motor by a typical eye length simultaneously with addition of the lens, so as to quickly switch between retinal and corneal OCT imaging.

When using this method, the iris view and LSO image are not disturbed, and the patient continues to see the fixation target.

Method for Combining B-Scans ("Thick B-Scan")

SD-OCT greatly enhances data acquisition speed by simultaneously acquiring position and scattering intensities for all scatterers along an A-Scan. The time savings may be used to simply allow faster completion of the same exams or the time may be used to acquire more data, such as acquisition of higher density volumes. Acquisition of more data provides the opportunity to combine data in order to improve some feature or parameter, such as combining data by spatially compounding in order to reduce speckle. OCT-tomograms generally suffer from degraded image clarity due to image speckle and noise. Structures whose dimensions approach the resolution limit of the imaging system display speckle discontinuities. For example, the external limiting membrane in retina cross sections shows speckle discontinuities when imaged using medium resolution OCT. Speckle reduction is generally achieved by compounding the image cell using various data acquired by means that vary the speckle property, generally either frequency compounding (by viewing the speckle generating cell by means of a different optical frequency) or spatial compounding (by viewing the speckle generating cell from a different spatial location, usually a different angle.) (See U.S. Pat. No. 6,847,449 and Schmitt, J. M., S. H. Xiang, et al. "Speckle in Optical Coherence Tomography." Journal of Biomedical Optics 4(1):95-105 (1999).) This embodiment describes a method of speckle reductions which combines elements of adjacent A-scans to produce a speckle reduced B-scan with reduced noise and enhanced visual impression. A B-scan resolution cell is a cell within the B-scan that is resolvable in the displayed image.

Figure 15A:
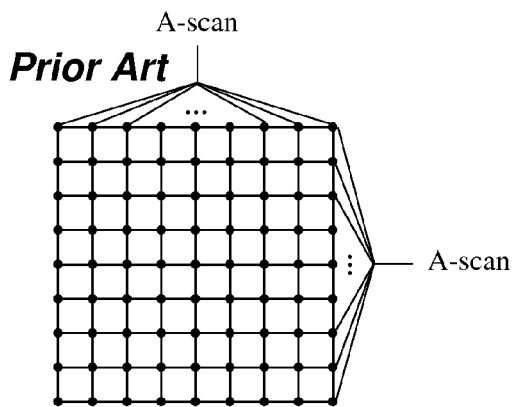
FIG. 15a illustrates a grid of A-scans for acquiring a 3-D OCT volume.
Figure 15B:
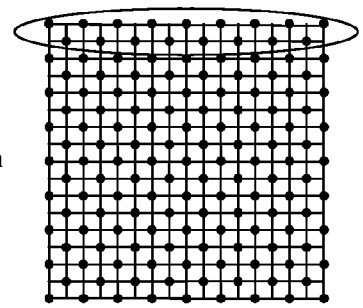
FIG. 15b illustrates a thick B-scan achieved by combining 2 B-scans.
Figure 15C:
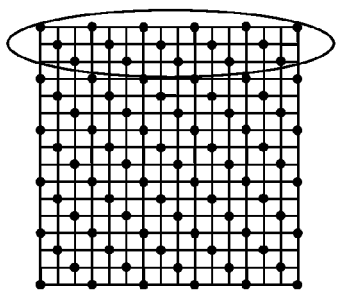
FIG. 15c illustrates a thick B-scan achieved by combining 3 horizontal B-scans.
Figure 15D:
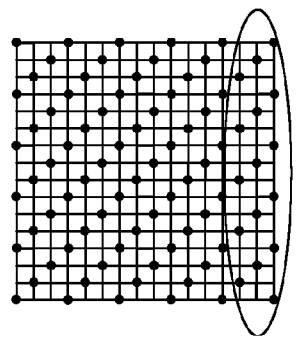
FIG. 15d illustrates a thick B-scan achieved by combining 3 vertical B-scans.

While this embodiment generally derives one or more A-scans from a collection of A-scans, its implementation and speckle reduction advantage is more easily described as a method of determining a B-scan from one or more B-scans. In its simplest instantiation, a single B-scan is created by over-sampling the image region. (While over-sampling the original B-scan is not necessary, it is easy to visualize compounding without resolution reduction using over-sampled data.) A new B-scan is derived from the image data of the acquired B-scan by laterally filtering the acquired B-scan at each depth. The new B-scan may be decimated either after or during the filtering step so that it is no longer over-sampled. The resulting B-scan is speckle reduced along the laterally filtered direction, but retains specular features acquired in the transverse direction (orthogonal to the B-scan). For transverse smoothing in the direction orthogonal to the B-scan (and the creation of a "thick B-Scan"), one or more adjacent B-scans can be used. Data at a fixed depth in an A-scan can be combined with data from the same depth in other A-scans. Algorithmically, these combinations are simpler when the B-scans are acquired in a fixed grid of parallel planes (B-scans), as in FIG. 15*a*. However, when combining data for speckle reduction, the resulting image contains fewer, or at least different, artifacts when the A-scans are not rigidly oriented on a regular grid. FIGS. 15 *a-d* are used to illustrate compounding B-scans. In FIGS. 15 *a-d*, the dots represent A-scans and lines represent B-scans. FIG. 15*a* shows the traditional scan pattern. In FIG. 15*b*, adjacent B-scans are acquired with the A-scan acquisition shifted by 50% of the spacing between A-scans in one of the B-scans. The shift of 50% of the spacing between A-scans is particularly advantageous when precisely two B-scans are used to acquire a new, interpolated B-scan. FIG. 15*c* represents combining three (3) rows to form a single B-scan while FIG. 15*d* shows three (3) columns being combined to form a single B-scan.

In general, A-scans from M rows and N columns can be combined to form a single computed A-scan. One method of combining is bi-linear interpolation. An alternative combination is obtained if a median filter is used. Alternatively, the value of any depth point in the computed A-scan can be viewed as a weighted sum of the neighboring A-scans. The weighted sum can include depth points. In general, the weights should be set so that the majority of the support for each computed pixel lies within one or two speckle diameters along each axis. The smaller the scope of this support, the greater the resolution (though this technique cannot improve the resolution beyond that of the imaging system), while the larger the scope of this support, the greater the speckle reduction. Two A-scans are speckle diverse if they are separated by approximately more than ½ the diameter of a speckle cell. Preferably speckle diverse A-scans are separated by a speckle diameter, however, smaller separations can achieve some speckle reduction. Similarly, a collection of A-scans are speckle diverse at a point in a direction if the collection contains A-scans which are separated by approximately more than ½ the diameter of a speckle cell in that direction. Again, preferably they are separated by a speckle diameter.

Figure 16A:
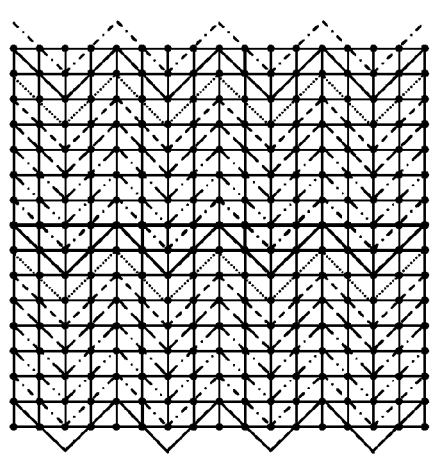
FIG. 16a illustrates a wiggle pattern for acquiring speckle reduced B-scans.
Figure 16B:
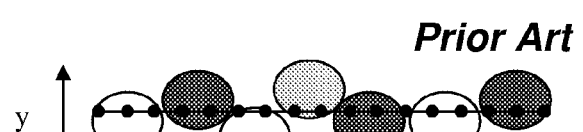
FIG. 16b illustrates how the A-scans of a traditional B-scan relate to speckle at a given depth.
Figure 16C:
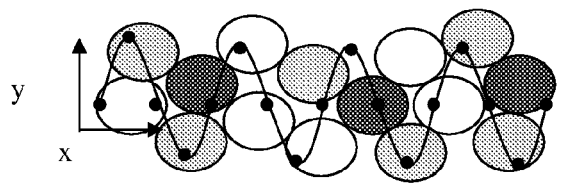
FIG. 16c illustrates how the A-scans acquired for speckle reduced B-scans relate to speckle at a given depth.

The combination can be performed either during acquisition or post acquisition. FIGS. 16*a* and 16*c* represent patterns expressly designed for combination during acquisition. FIG. 16*b* is included to depict the difference in the data collected using the prior art acquisition sequence 16*b* and the embodiment of the invention depicted in FIG. 16*c*. Here the A-scan locations wiggle (are dithered) about a centerline. The span of the wiggle is greater than a speckle diameter, as shown in FIG. 16*c*. As depicted, any 4 A-scans are speckle diverse both tangent to and orthogonal to any plane orthogonal to the y-axis. Here the compounding can be performed during acquisition with only a required memory of a few A-scans. Combination can limit computation by using a simple FIR filter, such as a boxcar or lowpass filter, or non-linear filter, such as a median filter. Combinations may also use be complex, using higher order statistics derived from neighboring A-scans. The primary advantage of compounding during acquisition is that the data is acquired at sufficiently high speed that motion during acquisition can be ignored. For the target SD-OCT system described herein, typical modulation parameters are nominally on the order of 10 µm for the period of the wiggle and 10 µm amplitude. A range of 5-20 µm is typical. Clearly, any differences in the system design affecting the resultant speckle size would also affect the nominal modulation parameters.

The deliberate decrease of discrimination in the orthogonal direction to a B-scan may constitute a new OCT display modality of tomographic data ("thick B-scan"). The thick B-scan modality is useful for viewing layer-like structures with a thickness close to the speckle limit. Further new displays combine the thick B-scan and one or more standard B-scans. For example, a thick B-scan derived from data from three (3) B-scan planes, say B1, B2, and B3, can be displayed essentially also showing $B_1$, $B_2$, and $B_3$. We display the intensity of the thick B-scan with the hue determined by $B_1$, $B_2$, and $B_3$; where the hue is blue if the intensity of $B_1$ is closest to that of the thick B-scan, the hue is yellow if the intensity of $B_2$ is closest to that of the thick B-scan, and the hue is red if the intensity of $B_3$ is closest to that of the thick B-scan. Any such display provides a suitable presentation of the deviation of the contributing B-scans from the combined one and can even offer some spatial interpretation of the two dimensional data even in a printed version.

This embodiment enables the selection of a B-scan with: reduced speckle and noise; no significant loss in lateral resolution in the direction of the B-scan; no increase in the number of detectors or, in some cases, scan-time; optionally increased density of A-scans in the presented B-scan; and optionally adjustable lateral resolution orthogonal to the B-scan direction. While B-scans are nominally thought of as planar sections, they can be any curved surface. The most typical B-scans are planar cross-sections and circle scans. Circle scans are scans covering a cylindrical surface whose perpendicular cross sections are nominally circular. Circle scans are particularly useful for determining retinal nerve fiber layer health, where the macular nerve head lies within the circle scan (nominally at the center of the cylindrical surface of the B-scan.)

Adaptive Compensation of Galvo Response

The motors of optical scanning galvanometers ("galvos") mechanically wear out after being scanned back and forth many times (up to billions of cycles). Before they fail completely and catastrophically, their bearings and lubricants may deteriorate gradually over a long period of time. These motors are typically driven by servo amplifiers that attempt to minimize the difference between the actual galvo motor position and a commanded position, provided as either an analog or a digital signal. In ophthalmic scanning, image quality and repeatability is directly dependent on galvo performance.

Two embodiments which ensure consistent scanning performance (i.e. consistent position response for a given command sequence) over the lifetime of an application are:

1) Characterize the closed-loop response and adapt the loop filter of the servo in order to keep the closed-loop response constant, and
2) Characterize the closed-loop response of the galvo system and adapt the command signal given in order to achieve the desired position response.

In both of these embodiments, it is essential to characterize the complete closed-loop response of the system. This can be done, for example, by having some software on an instrument that gives a white noise command to each galvo and digitizes the position response. The Fourier transform of the position response would provide the closed-loop frequency response.

In approach 1), a mechanism is needed to adjust the tuning of the servo filter. If the servo is digital, this can be accomplished using software running on an instrument. This can also be accomplished if the servo is analog but has digitally settable potentiometers in the servo circuit. Appropriate adaptive filter algorithms can be achieved using known techniques.

In approach 2), the closed-loop response is allowed to change over time. The desired command signal at any given time can be determined by applying the inverse of the closed-loop response to the desired position response.

In practice, it is best to utilize high-acceleration, asymmetric galvo waveforms for the purpose of "clearing" the galvo motors. These waveforms are designed to cause the balls in the galvo bearings to skid to a new position and avoid pit formation where the balls rock back and forth in the galvo raceways. Reliability testing has shown that these clearing moves can prolong the life and performance of the galvos.

Calibration Test Eye

In order to align, calibrate and test an ophthalmic instrument, it is desirable to have an artificial test eye. Various artificial eyes have been used throughout the ophthalmic industry, some very simple with poor imaging quality, others are more complicated, imitating the structure of the human eye (cornea and lens) and achieving high optical quality at great cost.

Figure 17:
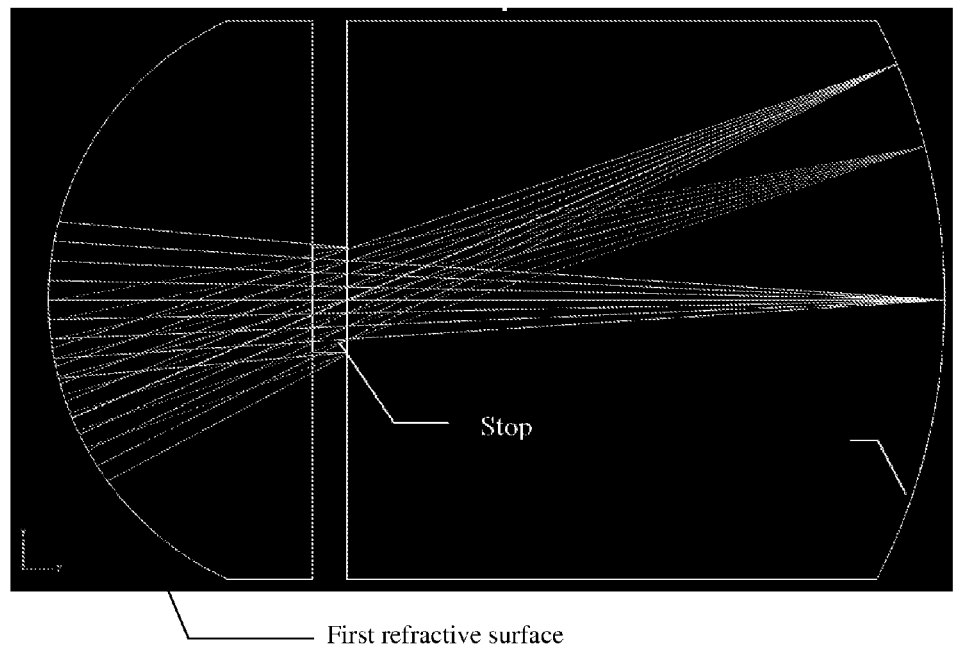
FIG. 17 illustrates the Optical lay out of a test eye.

FIG. 17 illustrates a test eye using one single refractive surface and a stop. This arrangement achieves very high optical quality over a 47-degree full field of view.

One embodiment is obtained using a single piece of optical glass, with a stop placed in the center of curvature of the first surface to avoid coma, astigmatism and lateral color. The imaging surface is curved to match field curvature and any pattern on the imaging surface is graduated in arc-mm to compensate for the distortion.

An alternate embodiment is obtained using aspheric surfaces to further reduce spherical aberration.

Co-Focus of Fundus Imager and Fixation Target

Ophthalmic instruments imaging the retina (fundus camera, LSLO, CSLO, OCT) use an internal fixation target to align the eye. It is desirable to co-focus the imaging optical path with the internal test target optical path so that the fundus image seen by the optician is in focus at the same time as the fixation target seen by the patient. The following paragraphs describe a method and apparatus which achieves this result.

Figure 18:
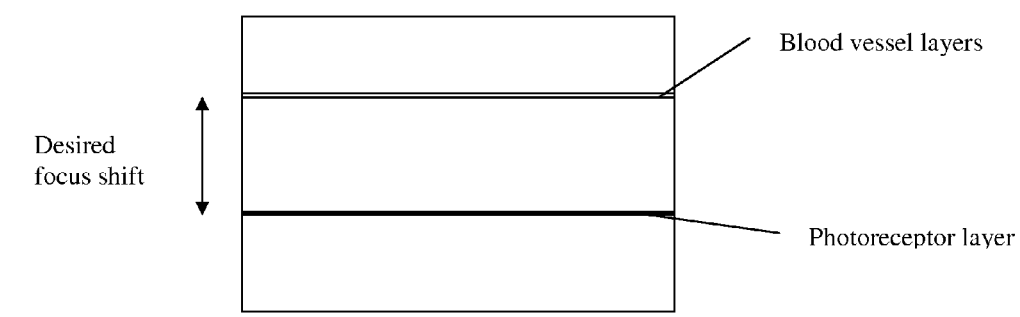
FIG. 18 illustrates the cross section of a retina.

Standard practice is to focus the imaging path and the fixation path in the same plane. FIG. 18 illustrates the preferred focus described herein. In this embodiment, the preferred focus of the fundus imager is anterior to the photoreceptor layer of the eye. The preferred focus for the fundus imager is at the blood vessel layer, while the preferred focus for the fixation target is at the photoreceptor layer. Therefore, we focus the imaging path and the fixation path in different planes separated by a distance. This enables the patient to see a sharper fixation target during the eye examination when the fundus is being imaged by the doctor. The sharper fundus image improves the patient's attention on the fixation target, thereby decreasing eye motion and creating a higher quality fundus image by reducing motion artifacts.

The standard design of camera lenses achieves near zero longitudinal aberration across all wavelengths within its design parameters. One embodiment achieves the desired result by implementing a camera lens with a known positive longitudinal chromatic aberration. That is, the lens longitudinal aberration is the sum of human eye chromatic aberration and the desired focus shift at the specified wavelength.

Figure 19A:
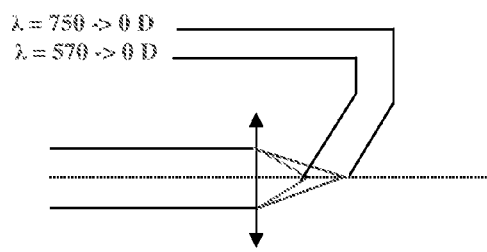
FIG. 19a illustrates the traditional optical alignment of two optical devices without chromatic aberration alignment.
Figure 19B:
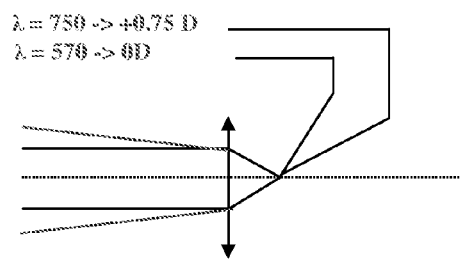
FIG. 19b illustrates the traditional optical alignment of two optical devices with chromatic aberration alignment.
Figure 19C:
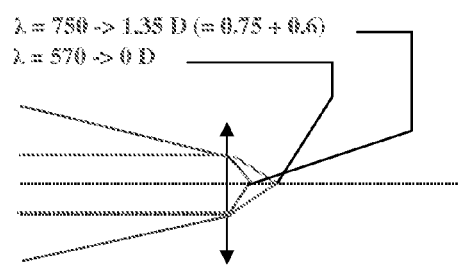
FIG. 19c illustrates the preferred optical alignment of two optical devices with chromatic aberration alignment.

FIGS. 19 a-c compare an ophthalmic instrument aligned with the prior art approach to an ophthalmic instrument aligned using the disclosed method. FIG. 19a shows the actual alignment of the Prior Art system with a fundus imaging system and a fixation target which is not chromatically aligned. The vertical arrow of FIGS. 19 a-c represents the refractive power of the cornea and crystalline lens, combined as a single lens. While the system is ostensibly designed to focus both the fundus imager and the fixation target systems in the same plane, because the chromatic aberration of the eye optical components is not accounted for, the actual focus has the infrared fundus imager focus posterior to the visible fixation target. That is, the focus of the fundus imaging system is too deep. FIG. 19b shows the same system with the fundus imaging system properly chromatically aligned, but without the preferred fundus imaging focus alignment. FIG. 19c shows the same system with the preferred fundus imaging focus alignment. The desired alignment can be accomplished during manufacturing either by using different lenses for aligning different optical systems or a single lens with the desired optical properties of each system. The first alternative has the advantage of utilizing readily available lenses and the disadvantage of changing lenses during final system alignment. The latter alternative has the advantage of not requiring manufacturing to change lenses in the test fixture during alignment with the disadvantage of requiring a special purpose lens which may require re-design in case of system component changes. FIG. 19c provides the design parameters for one such special purpose lens Other imaging systems combined in one instrument are commonly aligned in a common plane in the prior art and can also benefit from further embodiments of this invention. For instance, in color fundus cameras with imaging arrays, multiple sensors are used for different wavelengths of illumination. In those cases, it is possible to adjust the axial positions of the sensors relative to each other, so that each sensor is optically conjugate to the source of scattered light. If light from all wavelengths is scattered from the same depths, then the optical system is compensating for chromatic aberration to have all wavelengths at the best focus simultaneously. Alternatively, one sensor configured to receive visible light may be conjugate to layers anterior to the retinal pigment epithelium, and a sensor configured to receive near-infrared light may be conjugate to the choroidal blood vessels posterior to the retinal pigment epithelium. Therefore, different layers of the retina may be imaged on different sensors simultaneously.

In the case of retinal OCT systems, a fundus camera and confocal scanning optics provide simultaneous imaging of the retina. For example, the Stratus OCT (Carl Zeiss Meditec, Inc., Dublin, Calif.) employs a fundus viewing system that is color-corrected so that both the OCT beam and fundus viewer, for a range of visible and near-infrared wavelengths, are both conjugate to the same depth in the retina.

Scanning imagers, such OCT scanners, may not provide sufficient speed to produce real-time images to allow technicians to align the OCT scan area with the desired region to be imaged, for instance the foveal region of the retina. To assist this placement, a continuously displayed image of the retina is desired. Illumination with near-infrared light, for instance in the range of 700-900 nm, provides an image of the fundus without causing patient discomfort and/or constriction of the pupil. The scattering efficiency and absorption in the retinal layers above the RPE is relatively low in the near infra-red. Therefore, it is difficult to produce images of retina in these layers with near infra-red light. However, these layers are clinically very important, for instance to characterize retinal pathologies such as macular holes, and scanning systems, such as OCT, are often focused on these layers.

One option is to provide an infra-red fundus viewer, such as with an array sensor in a configuration similar to that in Stratus OCT. The infra-red image in this case has the best contrast below the RPE, where the choroidal vessels are imaged. Therefore, the fundus viewer is adjusted so that it is conjugate to the choroidal vessels when the OCT scanner is conjugate either to the RPE or to layers anterior to the RPE such as the inner plexiform layer. This can be achieved, for instance, by first adjusting the OCT and fundus viewers to be conjugate to the same layer in the retina or to a test fixture, then by shifting the axial location of the fundus viewer sensor so that it is conjugate a specific distance posterior to the RPE corresponding to tissue posterior to the RPE. This distance would typically be in the range of 0.2 to 1.0 mm. For example, in reference to U.S. Pat. No. 7,140,730 B, FIG. 3, the CCD could be shifted along the optical axis as described above. Alternatives to the alignment method, such as using a flip-in spacer to make the adjustments, and alternatives to the design adjustment, such as shifting lenses instead of the sensor, are obvious to those skilled in the art. Providing best focus at different depths simultaneously offers two advantages. First, the best focus of the fundus image, occurring posterior to the RPE, corresponds to the best focus of the OCT scanner at the desired depth so that the user can use cues from the fundus image, such as the sharpness of the image, to adjust the focus of the OCT. Second, the fundus image provides the best possible features for use as landmarks in placing OCT scans.

Another option is to provide two scanning imaging systems. The first system, such as an OCT scanner, is slower than the second system, such as a scanning laser ophthalmoscope (SLO), a line scanning laser ophthalmoscope (LSLO), or a line scanning ophthalmoscope (LSO). The second system provides video-rate images of the area to be scanned, such as the foveal region of the retina. When the second system is a confocal imager, even near-infrared light can be used to provide good contrast images of the blood vessels anterior to the RPE. To improve the contrast and sharpness of those images further, the second scanner is adjusted so that it is conjugate to a layer somewhat anterior to conjugate of the first scanner. For example, the second system may be conjugate to blood vessels anterior to the RPE when the first system is conjugate to the RPE layer. This offset is typically in the range of 0.2-0.5 mm depending on the expected state of pathology in the eye.

Another option is to provide an infra-red fundus viewer, such as with an array sensor, with an OCT scanner in a configuration similar to that in Stratus OCT, where both the fundus viewer and OCT scanner are optically conjugate to the same layer. The new instrument achieves the desired separation of focal planes by first aligning the infra-red fundus viewer to its best focus on the choroid (tissue posterior to the RPE). When you are ready to capture OCT data, we then automatically shift the focus of both the infra-red fundus viewer and the scanner to the desired scan depth. This shift can be achieved, for instance, by motorizing at least one of the two imagers and then using the motor to shift the sensor or a lens axially before acquiring the scanned image. Alternatively, this focal shift can be accomplished by flipping in a lens or swapping out one lens for another to shift the focal plane the desired distance.

Figure 20:
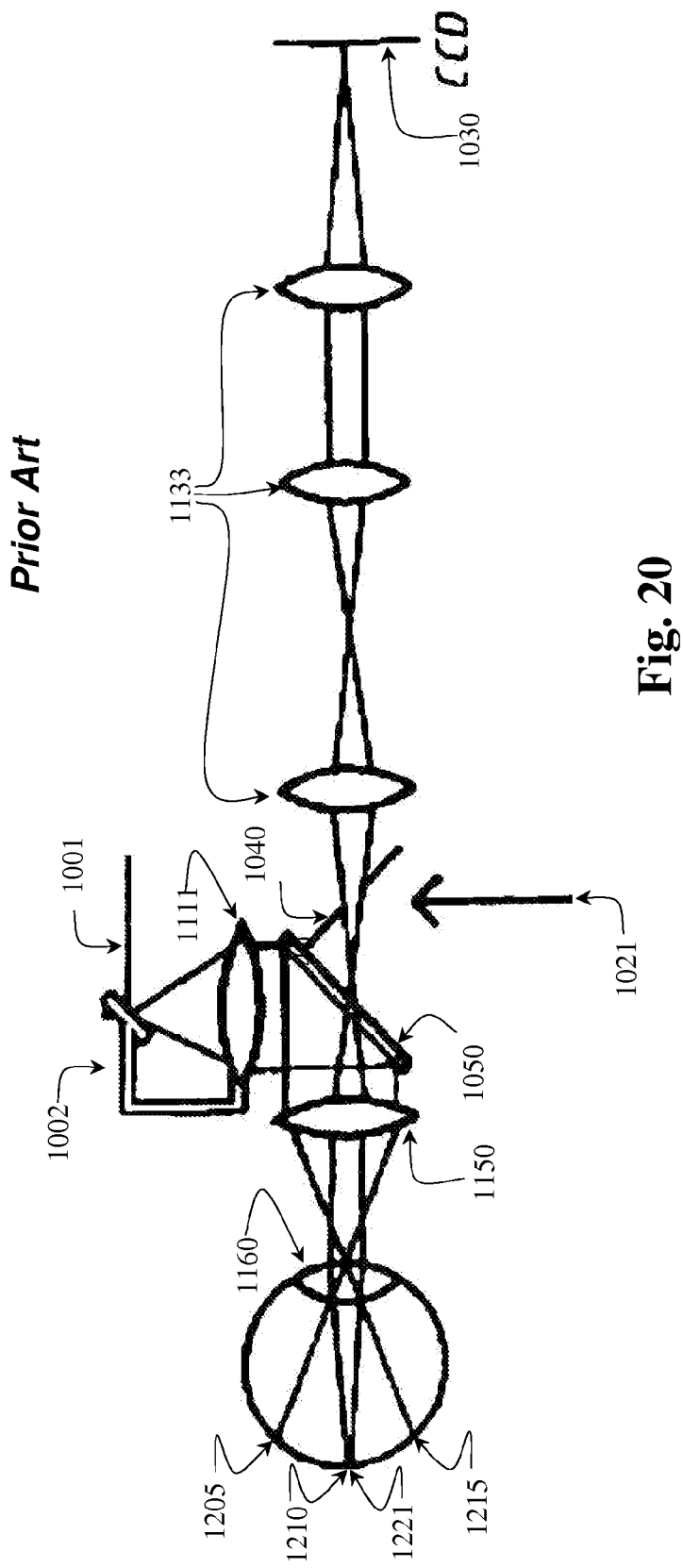
FIG. 20 shows, in pictorial form, a conventional scanning optical system and fundus camera.

FIG. 20 shows, in pictorial form, a conventional arrangement of two imaging subsystems. A scanning imaging subsystem includes a pencil beam light source 1001 and scanning mechanism 1002, scanning lens 1111, chromatic beam splitter 1050, focusing lens 1150, lens of the eye 1160 and a scanning area which sweeps out a surface bounded above by 1205, bounded below by 1215 and including focal point 1210. As the scanning mechanism sweeps the pencil beam across the scanning area, the focal point 1210 moves about a region on the retina. A second imaging subsystem is a fundus camera with area illumination light source 1021 and beam splitter 1040 (in this case depicted by a pin-hole minor). The second imaging system includes, common to the scanning imaging subsystem, optics path elements: chromatic beam splitter 1050 focusing lens 1150, lens of the eye 1160 and a surface of points near the retina, including point 1221, which will be brought to focus on detector 1030. When one says that the two imaging systems are focused at the same plane, what is meant is that the scanning area swept by the scanning imager is essentially the same (or contains or is contained in) surface which the second imaging systems brings into focus at detector 1030. Lens system 1133 functions to focus the fundus camera image on the CCD camera detector 1030.

In one embodiment of the current invention, the CCD camera detector 1030 is moved to be conjugate to a point posterior to 1210.

Figure 21:
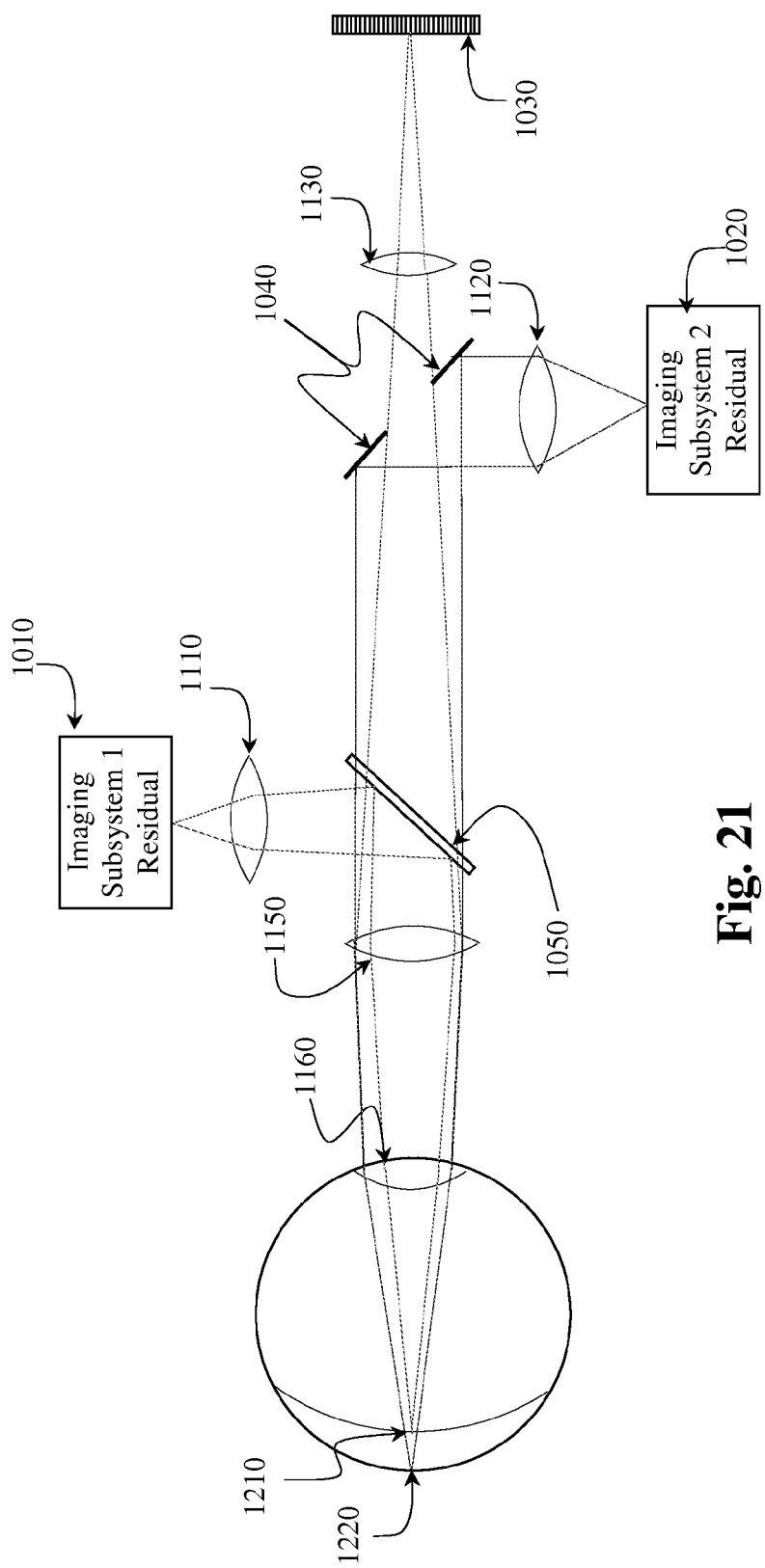
FIG. 21 shows, in pictorial form, one embodiment of the current invention.

FIG. 21 illustrates an arrangement of two imaging subsystems. The residual portion of the first imaging system which is not depicted resides in 1010. This can be a beam imaging system, either scanning or fixed, or an area illuminating light source, like a fundus illuminating source. The residual portion of the second imaging system which is not depicted resides in 1020. This can also be a beam imaging system, either scanning or fixed, or a line or area illuminating light source, like an SLO or fundus illuminating source, respectively. The first imaging subsystem is conjugate to the focus at 1210 while the second imaging subsystem is conjugate to the focus at 1220. The lens of the eye 1160, the lens 1150, and one side of the chromatic beam splitter 1050 are part of a common optical path for both subsystems. Lens 1110 completes the focus so that the first imaging subsystem is conjugate to 1210. Lenses 1120 and 1130 complete the focus of the second imaging subsystem so that detector 1030 is conjugate to 1220. Beam splitter 1040 (here depicted as a pin-hole minor) acts to redirect the source for the second imaging subsystem to align with the common optical path, while allowing reflected light back to detector 1030.

Figure 22:
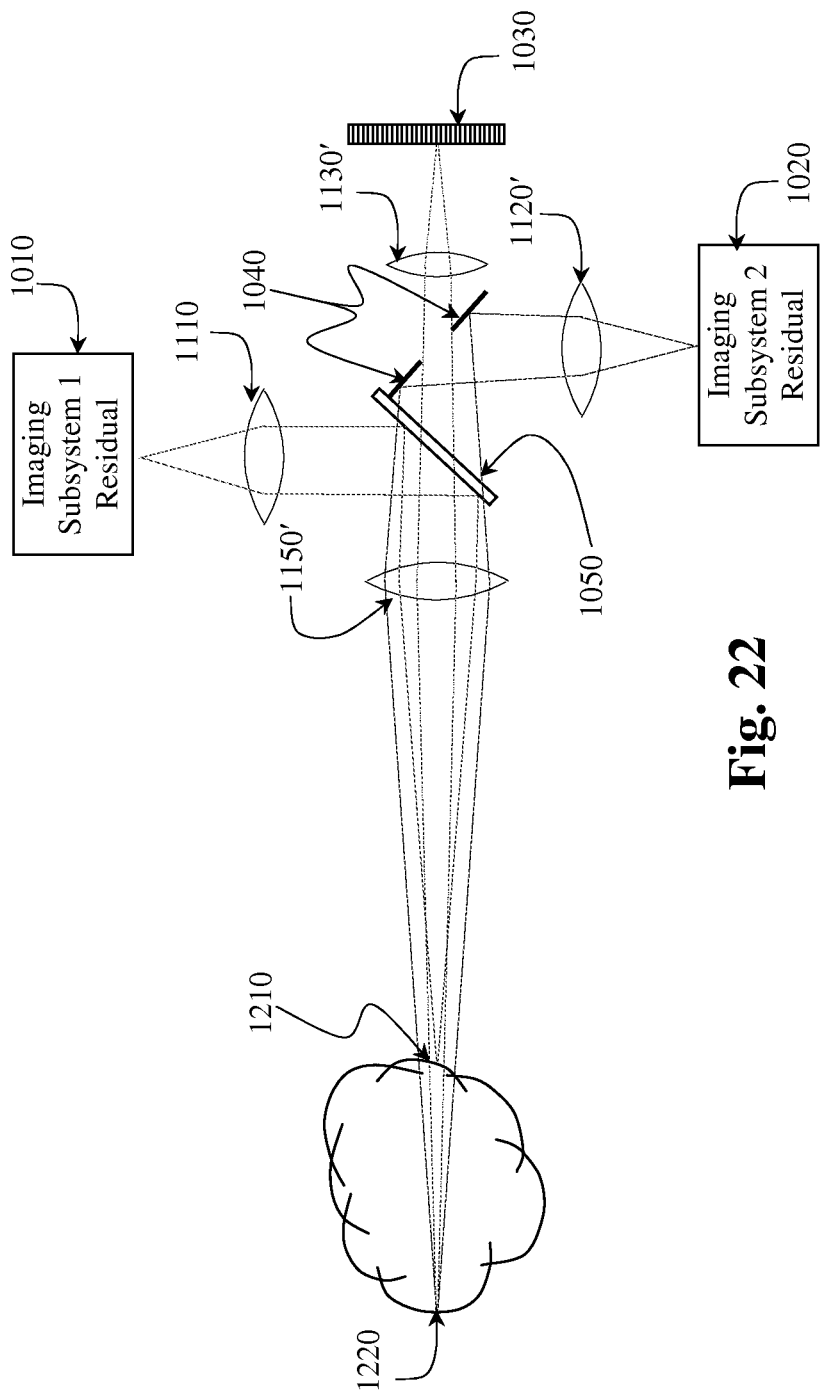
FIG. 22 shows, in pictorial form, another embodiment of the current invention.

FIG. 22 illustrates a simplification of FIG. 21. The effect of lenses 1150 and 1160 are combined into lens 1150'. The lens 1120 is replaced by lens 1120' so that the light is not collimated at the pinhole mirror. Lens 1130 is replaced with lens 1130' so that 1220 is conjugate to detector 1030. Lens 1110 is replaced with lens 1110' so that 1210 is conjugate to the detector of the first imaging subsystem.

Figure 23:
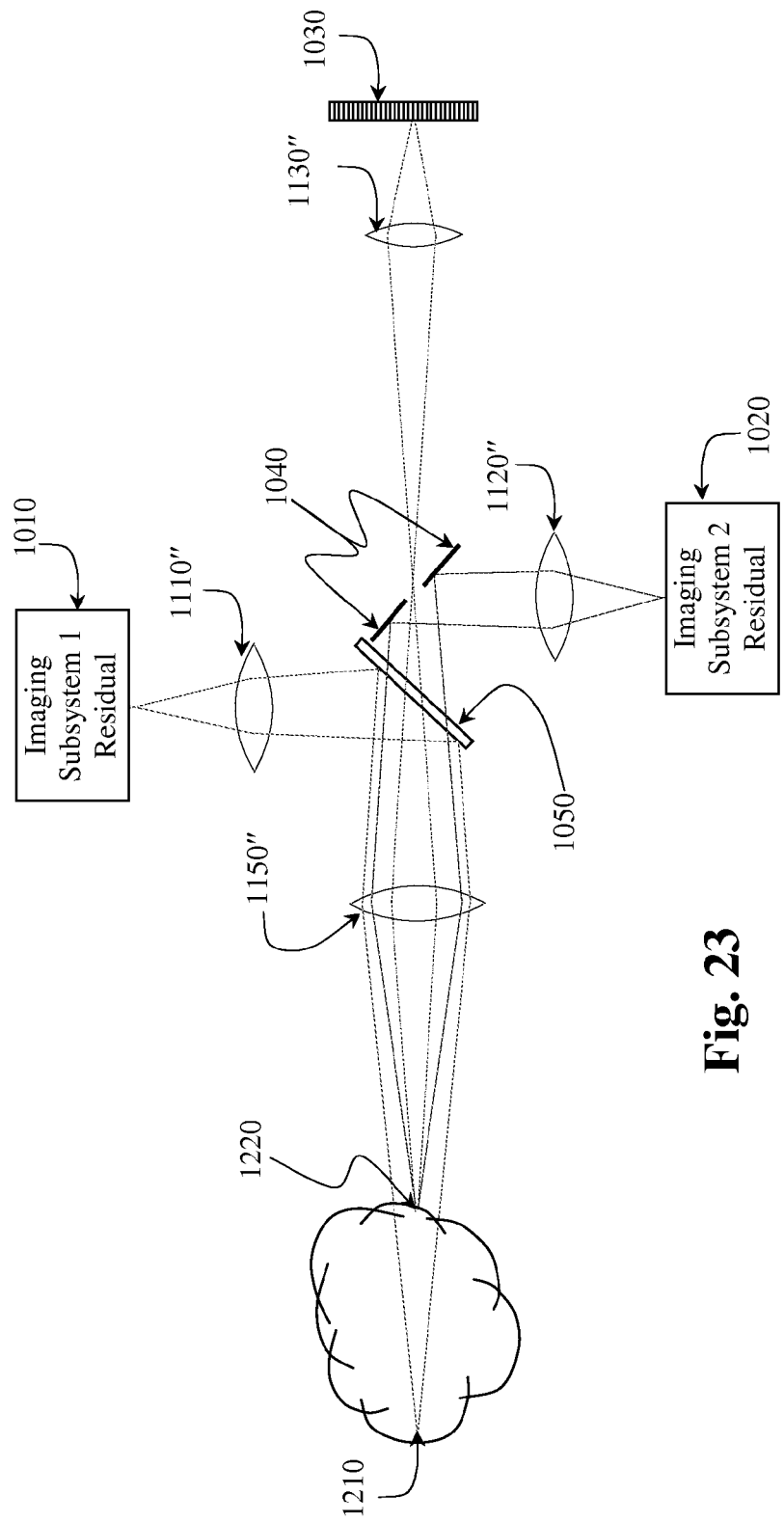
FIG. 23 shows, in pictorial form, yet another embodiment of the current invention.

FIG. 23 illustrates yet another configuration of the invention. Here the second imaging subsystem focuses anterior to the focus of the first imaging subsystem in order to illustrate that either subsystem can image anterior to the other. The lens 1150' is replaced by lens 1150", so that 1220 is essentially conjugate to the pinhole minor. Lenses 1120" and 1130" are consistent with lens 1150' and are designed so that 1220 is conjugate to detector 1030. Lens 1110" is consistent with lens 1150' and is designed so that 1210 is conjugate to the detector of the first imaging subsystem.

In FIGS. 21, 22, and 23, only the configuration is shown, where the focal points 1210 and 1220 are not aligned. As previously described, this can be accomplished in various ways, including the changing out of lenses or movement of the detector.

It should be understood that the embodiments, examples and descriptions have been chosen and described in order to illustrate the principals of the invention and its practical applications and not as a definition of the invention. Modifications and variations of the invention will be apparent to those skilled in the art. The scope of the invention is defined by the claims, which includes known equivalents and unforeseeable equivalents at the time of filing of this application.

What is claimed is:

1. A method of generating a cross-sectional image of a surface within a tissue using an optical coherence tomography (OCT) system comprising:

acquiring a plurality of OCT A-scans from within the tissue, at least some of the A-scans being orthogonally displaced from the surface to be imaged;

generating a cross-sectional image of the surface within the tissue by compounding a plurality of A-scans, wherein at least a subset of the A-scans are selected from positions displaced orthogonally with respect to the surface, such that speckle in the cross-sectional image is reduced compared to a cross-sectional image generated only from A-scans along the surface; and displaying or storing the resulting cross-sectional image.

2. A method as recited in claim 1, wherein two or more of the plurality of A-scans are separated by at least approximately half a diameter of a speckle cell.

3. A method as recited in claim 1, wherein two or more of the plurality of A-scans are separated by at least approximately a full diameter of a speckle cell.

4. A method as recited in claim 1, wherein two or more of the plurality of A-scans are separated by between approximately 5 and approximately 20 microns.

5. A method as recited in claim 1, wherein the cross-sectional image corresponds to a substantially planar surface in the tissue.

6. A method as recited in claim 1, wherein the cross sectional image corresponds to a substantially cylindrical surface in the tissue.

7. A method as recited in claim 1, wherein the cross sectional image corresponds to a curved surface in the tissue.

8. A method as recited in claim 1, wherein the compounding step includes bi-linear interpolation of two or more of the plurality of A-scans.

9. A method as recited in claim 1, wherein the compounding step includes median filtering of two or more of the plurality of A-scans.

10. A method as recited in claim 1, wherein the compounding step includes weighted summing of two or more of the plurality of A-scans.

11. An optical coherence tomography (OCT) system, the OCT system including a light source generating a light beam, a sample arm, a reference arm and a detection arm, said OCT system for generating a cross sectional image of a surface within a tissue, said OCT system comprising:

optics for scanning the light beam to a plurality of positions in an X/Y plane;

a detector coupled to the detection arm for generating output signals in response to light collected from the sample arm and the reference arm and wherein an A-scan corresponds to a reflectance distribution as a function of depth (Z) at each X and Y position; and a processor for controlling the scanning optics and for receiving the output signals generated by the detector, said processor operating to acquire a plurality of OCT A-scans within the tissue, at least some of the A-scans being orthogonally displaced from the surface to be imaged, said processor generating a cross-sectional image of a surface within tissue by compounding a plurality of A-scans such that speckle is reduced compared to a cross-sectional image generated only from A-scans along the surface.

12. An apparatus as recited in claim 11, further comprising a display for displaying the generated cross-sectional image.

13. An apparatus as recited in claim 11, wherein two or more of the plurality of A-scans are separated by at least approximately half a diameter of a speckle cell.

14. An apparatus as recited in claim 11, wherein two or more of the plurality of A-scans are separated by at least approximately a full diameter of a speckle cell.

15. An apparatus as recited in claim 11, wherein t two or more of the compounded A-scans are separated by between approximately 5 and approximately 20 microns.

16. An apparatus as recited in claim 11, wherein the cross-sectional image corresponds to a substantially planar surface in the tissue.

17. An apparatus as recited in claim 11, wherein the cross sectional image corresponds to a substantially cylindrical surface in the tissue.

18. An apparatus as recited in claim 11, wherein the cross sectional image corresponds to a curved surface in the tissue.

19. An apparatus as recited in claim 11, wherein the combining step includes bi-linear interpolation of two or more of the plurality of A-scans.

20. An apparatus as recited in claim 11, wherein the combining step includes median filtering of two or more of the plurality of A-scans.

21. An apparatus as recited in claim 11, wherein the combining step includes weighted summing of two or more of the plurality of A-scans.

22. A method of generating and displaying a cross-sectional image of a surface of a tissue from a plurality of A-scans collected using an optical coherence tomography device, said method comprising
compounding a plurality of A-scans to generate a plurality of computed A-scans, wherein at least one of the A-scans being compounded in each computed A-scan is displaced orthogonally from the surface being imaged;
combining the computed A-scans to form a cross sectional image; and
displaying the cross-sectional image.

23. A method as recited in claim 22, wherein the resulting cross-sectional image has reduced speckle compared to a cross sectional image generated from only A-scans along the surface.

24. A method as recited in claim 22, wherein two or more of the plurality of A-scans are separated by at least approximately half a diameter of a speckle cell.

25. A method as recited in claim 22, wherein two or more of the plurality of A-scans are separated by at least approximately a full diameter of a speckle cell.

26. A method as recited in claim 22, wherein two or more of the plurality of A-scans are separated by between approximately 5 and approximately 20 microns.

27. A method as recited in claim 22, wherein the cross-sectional image corresponds to a substantially planar surface in the tissue.

28. A method as recited in claim 22, wherein the cross sectional image corresponds to a substantially cylindrical surface in the tissue.

29. A method as recited in claim 22, wherein the cross sectional image corresponds to a curved surface in the tissue.

30. A method as recited in claim 22, wherein the compounding step includes bi-linear interpolation of two or more of the plurality of A-scans.

31. A method as recited in claim 22, wherein the compounding step includes median filtering of two or more of the plurality of A-scans.

32. A method as recited in claim 22, wherein the compounding step includes weighted summing of two or more of the plurality of A-scans.

* * * * *

UNITED STATES PATENT AND TRADEMARK OFFICE
CERTIFICATE OF CORRECTION

| | |
|---|---|
| PATENT NO. | : 8,705,048 B2 |
| APPLICATION NO. | : 13/857675 |
| DATED | : April 22, 2014 |
| INVENTOR(S) | : Matthew J. Everett et al. |

It is certified that error appears in the above-identified patent and that said Letters Patent is hereby corrected as shown below:

On Title page 2, Item (56) References Cited: under "OTHER PUBLICATIONS", in column 1, line 9, Delete ""Senstivity" and insert -- "Sensitivity --, therefor.

In the Specification:

In column 2, line 20, Delete "minor" and insert -- mirror --, therefor.

In column 4, line 55, Delete "minors" and insert -- mirrors --, therefor.

In column 6, line 26, Delete "eights" and insert -- eighths --, therefor.

In column 7, line 42, Delete "minor" and insert -- mirror --, therefor.

In column 8, line 48, Delete "and" and insert -- an --, therefor.

In column 11, line 28, Delete "minors" and insert -- mirrors --, therefor.

In column 11, line 48, Delete "minor" and insert -- mirror --, therefor.

In column 11, line 50, Delete "minors" and insert -- mirrors --, therefor.

In column 13, line 10, Delete "laser" and insert -- lase --, therefor.

In column 15, line 26-29, Delete "Adjustment minor...across sample 30." and insert the same on Col. 15, Line 25, after "path." as a continuation of the paragraph.

In column 15, line 26, Delete "minor" and insert -- mirror --, therefor.

In column 15, line 31, Delete "minors" and insert -- mirrors --, therefor.

Signed and Sealed this
Twenty-second Day of July, 2014

Michelle K. Lee
*Deputy Director of the United States Patent and Trademark Office*

CERTIFICATE OF CORRECTION (continued)
U.S. Pat. No. 8,705,048 B2

In column 15, line 52, Delete "minor" and insert -- mirror --, therefor.

In column 16, line 1, Delete "minor" and insert -- mirror --, therefor.

In column 16, line 19, Delete "minor" and insert -- mirror --, therefor.

In column 16, line 24, Delete "minor" and insert -- mirror --, therefor.

In column 16, line 26, Delete "minors" and insert -- mirrors --, therefor.

In column 16, line 35, Delete "minor" and insert -- mirror --, therefor.

In column 16, line 39, Delete "minor" and insert -- mirror --, therefor.

In column 16, line 47, Delete "minor" and insert -- mirror --, therefor.

In column 16, line 55, Delete "minors" and insert -- mirrors --, therefor.

In column 17, line 11, Delete "minors" and insert -- mirrors --, therefor.

In column 17, line 15, Delete "minor" and insert -- mirror --, therefor.

In column 17, line 19, Delete "minor" and insert -- mirror --, therefor.

In column 17, line 23, Delete "Minor" and insert -- Mirror --, therefor.

In column 18, line 26, Delete "form" and insert -- from --, therefor.

In column 20, line 38, Delete "minors" and insert -- mirrors --, therefor.

In column 20, line 40, Delete "minors" and insert -- mirrors --, therefor.

In column 25, line 21, Delete "lens" and insert -- lens. --, therefor.

In column 26, line 65, Delete "minor)." and insert -- mirror). --, therefor.

In column 27, line 31, Delete "minor)" and insert -- mirror) --, therefor.

In column 27, line 46, Delete "minor." and insert -- mirror. --, therefor.

In the Claims:

In column 29, line 1, In Claim 15, delete "t two" and insert -- two --, therefor.